United States Patent
Tang et al.

(10) Patent No.: US 11,351,256 B2
(45) Date of Patent: Jun. 7, 2022

(54) ROOM TEMPERATURE STABLE LYOPHILIZED PROTEIN

(71) Applicant: Regeneron Pharmaceuticals, Inc., Tarrytown, NY (US)

(72) Inventors: Xiaolin Tang, Old Tappan, NJ (US); David Brett Ludwig, New York, NY (US)

(73) Assignee: Regeneron Pharmaceuticals, Inc., Tarrytown, NY (US)

(*) Notice: Subject to any disclaimer, the term of this patent is extended or adjusted under 35 U.S.C. 154(b) by 0 days.

(21) Appl. No.: 15/727,457

(22) Filed: Oct. 6, 2017

(65) Prior Publication Data

US 2018/0099049 A1    Apr. 12, 2018

Related U.S. Application Data

(60) Provisional application No. 62/405,610, filed on Oct. 7, 2016.

(51) Int. Cl.
| | | |
|---|---|---|
| *A61K 39/395* | (2006.01) | |
| *A61K 9/08* | (2006.01) | |
| *A61K 9/00* | (2006.01) | |
| *A61J 1/14* | (2006.01) | |
| *A61K 9/19* | (2006.01) | |
| *A61K 47/02* | (2006.01) | |
| *A61K 47/10* | (2017.01) | |
| *A61K 47/18* | (2017.01) | |
| *A61K 47/26* | (2006.01) | |
| *A61K 38/00* | (2006.01) | |

(52) U.S. Cl.
CPC ........ *A61K 39/39591* (2013.01); *A61J 1/1412* (2013.01); *A61K 9/0019* (2013.01); *A61K 9/08* (2013.01); *A61K 9/19* (2013.01); *A61K 47/02* (2013.01); *A61K 47/10* (2013.01); *A61K 47/183* (2013.01); *A61K 47/26* (2013.01); *A61K 38/00* (2013.01)

(58) Field of Classification Search
None
See application file for complete search history.

(56) References Cited

U.S. PATENT DOCUMENTS

| 5,798,032 A | * | 8/1998 | Khan | G01N 27/44773 |
| | | | | 204/450 |
| 2012/0114646 A1 | * | 5/2012 | Tchessalov | A61P 37/00 |
| | | | | 424/134.1 |
| 2014/0271636 A1 | * | 9/2014 | Rast | A61K 9/19 |
| | | | | 424/133.1 |

FOREIGN PATENT DOCUMENTS

| WO | 19/004801 A1 | 2/1997 |
| WO | 10/148337 A1 | 12/2010 |
| WO | 12/076670 A2 | 6/2012 |

OTHER PUBLICATIONS

U.S. Appl. No. 62/405,610, filed Oct. 7, 2016, Expired.
PCT/US2017/055651, Oct. 6, 2017, Pending.
WIPO Application No. PCT/US2017/055651, PCT International Search Report and Written Opinion of the International Searching Authority dated Jan. 8, 2018.
Chang et al., "Mechanism of Protein Stabilization by Sugars During Freeze-Drying and Storage: Native Structure Preservation, Specific Interaction, and/or Immobilization in a Glassy Matrix?" Journal of Pharmaceutical Science, vol. 94(No. 7), (Jul. 2005).
Nireesha et al., "Lyophilization/Freeze Drying—An Review," International Journal of Novel Trends in Pharmaceutical Sciences, vol. 3(No. 4), (Oct. 2013); ISSN 2277-2782.
Breen et al., "Effect of Moisture on the Stability of a Lyophilized Humanized Monoclonal Antibody Formulation," Pharmaceutical Research, vol. 18 (No. 9), (Sep. 2001).

* cited by examiner

*Primary Examiner* — Yunsoo Kim
(74) *Attorney, Agent, or Firm* — Kramer Levin Naftalis & Frankel LLP

(57) ABSTRACT

Stable lyophilized therapeutic protein compositions and their methods of manufacture are provided. Specifically, the use of water as a solid cake plasticizer and protein stabilizer is described. Also, the inclusion of a multicomponent stabilizer comprising a larger molecular entity and a smaller molecular entity is described. Also, the inclusion of post-drying annealing under certain conditions improves protein stability. Proteins are predicted to remain stable over 24 months at 25° C.

19 Claims, 2 Drawing Sheets

ROOM TEMPERATURE STABLE LYOPHILIZED PROTEIN

FIELD

Figure 1:
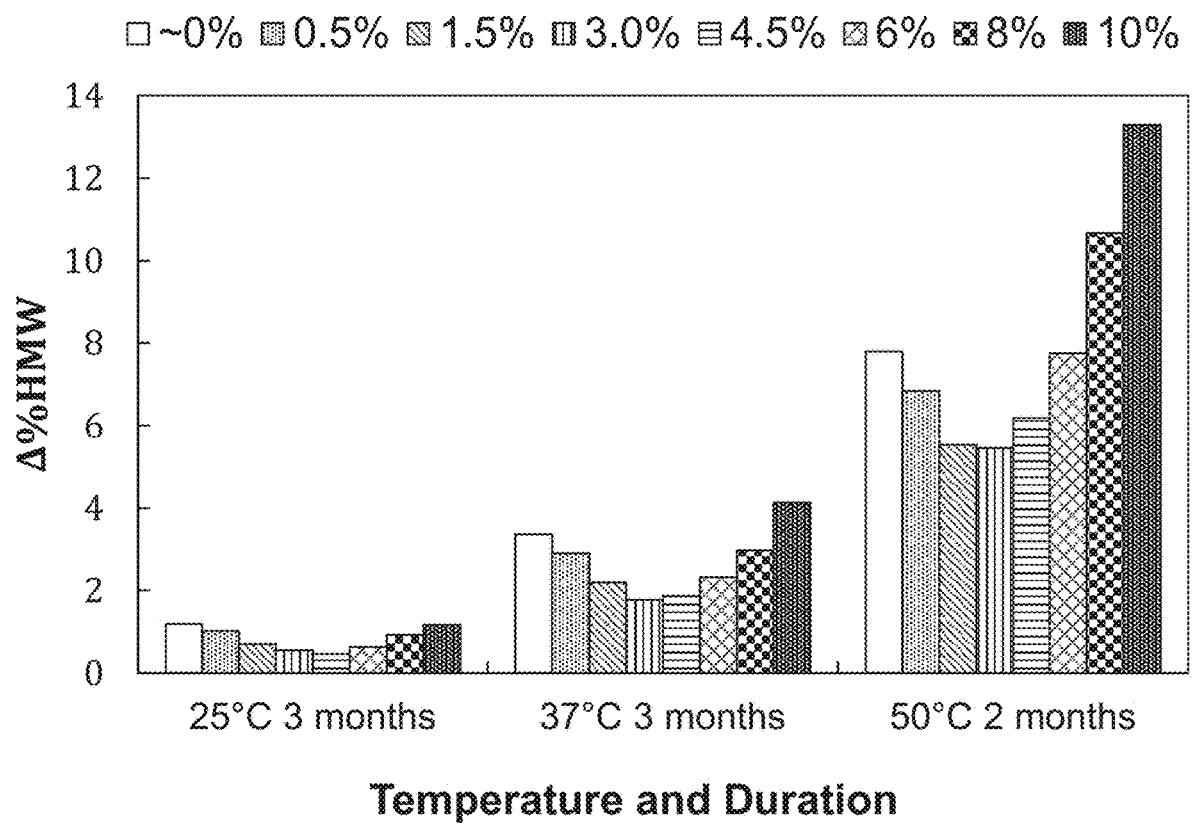

The present invention relates generally to the field of pharmaceutical formulation of biological molecules. Specifically, the present invention relates to stable lyophilized therapeutic protein formulations.

BACKGROUND

Therapeutic macromolecules, such as antibodies and receptor Fc-fusion proteins, must be formulated in a manner that not only makes the molecules suitable for administration to patients, but also maintains their stability during long term storage. For example, therapeutic proteins (e.g., antibodies) in liquid solution are prone to aggregation, chemical modifications, or other forms of degradation unless the solution is formulated properly. The stability of a therapeutic protein in liquid formulation depends not only on the kinds of excipients used in the formulation, and the amounts and proportions of those excipients relative to one another, but also on the concentration of the soluble protein and the method of manufacturing. Considerations aside from stability must also be taken into account when preparing a therapeutic protein formulation. Those considerations include the viscosity of the solution and the concentration of antibody that can be accommodated by a given formulation. Thus, when formulating a therapeutic protein, great care must be taken to arrive at a formulation that remains stable over time at storage temperature, contains an adequate concentration of antibody or other therapeutic protein, and possesses other properties which enable the formulation to be conveniently administered to patients.

Liquid formulations of therapeutic proteins are generally designed to provide long term stability to the protein when frozen or refrigerated, but often fail to provide long term stability at room temperature. One solution known in the art to preserve the stability and retain therapeutic activity of the protein is to lyophilize the molecule. Lyophilization (freeze drying under controlled conditions) is commonly used for long-term storage of proteins. The lyophilized protein is substantially resistant to degradation, such as, aggregation, oxidation, and other degenerative processes while in the freeze-dried state (see, for example, U.S. Pat. No. 6,436,897). Lyophilization provides a dry "cake" that remains relatively stable at room temperature for a relatively long period of time. Room temperature stability is especially important in storing and distributing therapeutic proteins around the world, especially in places where electricity and refrigeration are not reliable.

Lyoprotectants (a.k.a. stabilizers), such as sucrose and trehalose, are often included in pre-lyophilization formulations to protect the protein against denaturation during the freeze-drying process. Plasticizers may also be included to decrease global relaxation time and in some cases may help to preserve the native structure of proteins. Plasticizers include sugar alcohols like sorbitol and glycerol, other polyols, and small amounts of water.

In studies designed to optimize storage of lyophilized proteins at 5° C., Chang et al. investigated the effect of plasticizers on the stability of protein formulations. In lyophilization cakes that contained a weight ratio of 1:1 sucrose to protein (protein at 40 mg/mL pre-lyophilized) and no additional plasticizers the aggregation rate constant during a month at 50° C. was reportedly over 1.5% at 2.4% water content and around 2% at 3.3% water content (Id. at 1451, FIG. 4). ("Effect of Sorbitol and Residual Moisture on the Stability of Lyophilized Antibodies: Implications for the Mechanism of Protein Stabilization in the Solid State," J. Pharma. Sci. 94(7): 1445-1454, (2005). The experiment was also run for at 40° C. and 25° C. with data presented for only the harshest of the three stress conditions. Chang et al. noted rare examples of documented cases of optimal storage stability at intermediate moisture content and suggested that residual moisture content should be optimized during formulation development rather than something that simply has to be minimized. (Id. at 1451; see also Breen et. al., "Effect of Moisture on the Stability of a Lyophilized Humanized Monoclonal Antibody Formulation," Pharma. Res. 18(9): 1345-1353 (2001).) High moisture levels were shown in all of the studies cited by Chang et al. to decrease the chemical stability of the formulations. Hsu et al. "Determining the Optimum residual Moisture in Lyophilized Protein Pharmaceuticals," Develop. Biol. Standard 74:255-271 (1991).)

None of those studies suggest long term stability (over a year, two years, or three years or more) at a temperature above 5° C., let alone 25° C., even for the formulations tested.

Lyophilized formulations of biotherapeutic drugs have demonstrated long term stability under certain conditions. Kallmeyer et al., WO1998022136A2, describe stable lyophilized antibody formulations of low concentration (e.g., up to 8 mg/ml pre-lyophilized solution) that contain among other excipients a sugar (up to 200 mg/ml post-reconstitution [e.g., sucrose, lactose, maltose, raffinose, trehalose]), an amino acid (1-100 mg/ml pre-lyophilized [e.g., arginine, lysine, ornithine]), a surfactant (0.05 to 0.5 mg/ml post-reconstitution [e.g., polysorbates and polyoxyethylene-polyoxypropylene polymers]), and optionally a buffer (10-20 mM post-reconstitution [e.g., phosphate, acetate, citrate]) and/or an isotonizing agent (e.g., NaCl, no more than 30 mM post-reconstitution). Kallmeyer discloses that the lyophilizate that can be stored at room temperature (i.e., 18-23° C.) for up to two years while remaining stable. Here, stability is demonstrated by very low to no particulate formation in reconstituted lyophilizate, i.e., less than 6000 particles of more than 10 microns in size, or less than 600 particles of more than 25 microns in size.

Dix el al., WO2006104852A2, describe a stable lyophilized VEGF-Trap (a.k.a. aflibercept) formulation that maintains biological activity for at least three months. That application discloses the pre-lyophilized solution containing 5-75 mg/ml trap molecule, 5-50 mM histidine buffer, 0.1-3% polyethylene glycol (PEG; stabilizer), 0.25-3% glycine (as a bulking agent), and 0.5-6% sucrose (as a stabilizer). Optionally, the pre-lyophilized solution contains citrate buffer (0.05 mM) and/or 0.003% to 0.005% polysorbate.

In addition to lyophilized protein formulations, spray drying has also been employed to make dry protein formulations. Chen and Walsh (WO201307506A1) disclose dry micronized protein particles having a range of diameter of from two (2) to 30 microns, and a median diameter of about 10 to 12 microns, and in some cases about 6 to about 7 microns. These particles can be subsequently coated with polymer to further stabilize the protein and enable the extended release of the protein over time in an aqueous environment. The pre-processed protein solution from which the micronized particles were formed contained either (1) 25 mg/ml protein and 0.1% polysorbate, (2) 25 mg/ml protein, or (3) 50 mg/ml protein, 10 mM phosphate, and 2% sucrose. The protein contained within the polymer coated micronized protein particles were demonstrated to remain stable for at least 14 days.

Post-drying annealing of a protein lyophilizate was shown at 50° C. to result in an initial antibody aggregation to greater than 4% and the aggregation rate constant was about 2% aggregation per month. (See Wang et al., "The Impact of Thermal Treatment on the Stability of Freeze-Dried Amorphous Pharmaceuticals: II. Aggregation in an IgG1 Fusion Protein," 99(2) J. Pharma. Sci. 683-700 (2010).) While the US FDA might allow marketing of a formulation with initial aggregation at 4%, that rate of aggregation over time would be unacceptable for a marketed pharmaceutical formulation. There should be no visible change in a pharmaceutical formulation during its shelf life.

There remains a need for versatile dry protein formulations that remain stable over an extended period of time at room temperature. Versatile dry protein formulations are inter alia amenable to reconstitution for use as a liquid formulation, for combining with polymers to make extended release formulations or devices, and for implanting or delivering via a myriad of other routes. Here, Applicants have developed an improved stable protein lyophilizate and method of making it.

SUMMARY

A relatively high content of residual moisture can serve as an effective plasticizer for lyophilized therapeutic proteins (a.k.a. therapeutic proteins in the "solid state"), which offers surprising stability to the protein for at least 24 months while stored at room temperature. In one aspect, a room-temperature stable lyophilized therapeutic protein formulation in a low mobility solid state having between 0.5 and 10 percent moisture is provided. In another aspect, a method of making that room temperature stable, lyophilized therapeutic protein formulation is provided. In particular, residual moisture levels greater than 2%, greater than 3%, greater than 4%, greater than 5%, or greater than 6% in the lyophilization cake, but less than 10%, less than 8%, less than 7% or less than 6% allow annealing at relatively high temperatures for a prolonged period of time at room temperature. While not limited by any mechanism of action, the residual water content during the lyophilization process appears to permit alpha-relaxation to occur while preventing the formation of initial protein aggregates at relatively high concentrations of pharmaceutically formulation, preferably between 50-200 mg/ml, even more preferably between 100-150 mg/ml.

In a first aspect, a pharmaceutically acceptable lyophilized cake comprising a stable protein, an excipient, and from about 0.5% to about 10% water, from about 3% to about 6% water, from about 4% to about 7% water, from about 5% to about 8% water, about 3%, about 4%, about 4.5%, or about 6% water by weight is provided. The protein of the pharmaceutically acceptable lyophilized cake remains stable for at least one month at room temperature, which can be 17-25° C., 20-25° C., or at about 25° C. What is meant by "stable" in general is that less than 5%, less than 4%, less than 3%, less than 2%, less than 1% or very little to none of the protein is degraded within 18 months of storage at room temperature. A common degradation pathway for proteins is the formation of aggregates and other high molecular weight (HMW) species. HMW species can be detected by many known methods, such as size exclusion chromatography and native or denatured electrophoretic gel mobility, preferably by size exclusion chromatography. Degradation also includes the formation of chemical products such as deamidated residues, reduced disulfide bonds, hydrolysis and peptide fragmentation, and the like, that can also be measured by methods known in the art.

In one embodiment, less than or equal to about 2% of the protein is degraded following 24 months of storage at about 25° C. The degradation is determined by the percent change in high molecular weight species as measured by size exclusion chromatography. The lower limit of detectable degradation with this method is about 0.5% degradation, with about 0.2-0.3% as assay variability.

The pharmaceutically acceptable lyophilized cake can include one or more excipients in addition to the protein and the moisture. In one embodiment, the excipients include a buffer. That buffer can be any buffer that maintains the optimal pH for protein stability. Histidine is such a buffer, which has a pKa of about 6.0 and is capable of effectively buffering between pH 4.8 and 7.2. In some embodiments, the excipient is histidine. In a preferred embodiment, the histidine is present in a pharmaceutically acceptable lyophilized cake at about 0.34% to about 2.04% by weight.

In one embodiment, the excipients include a stabilizer. Stabilizers include various molecules such as polyols, sugars, amino acids, salts, or any combination thereof. Examples of useful stabilizers include sorbitol, glycerol, mannitol, trehalose, sucrose, arginine, alanine, proline, glycine, sodium chloride, or any combination thereof. In one embodiment, the stabilizer makes up from about 19.9% to about 82.2% of the weight of the pharmaceutically acceptable lyophilized cake.

The term "stabilizer" means at least one chemical entity that is not the buffer or the protein in a pharmaceutically acceptable lyophilized cake. In some embodiments, the term stabilizer means a combination of chemical entities (i.e., more than one chemical entity) that together serve to stabilize the protein or other macromolecule. For example, the stabilizer may be sucrose, or the stabilizer may be the combination of sucrose and arginine. In some embodiments, a larger molecular weight chemical entity, such as e.g. sucrose or trehalose, is paired with a smaller molecular weight chemical entity, such as e.g. arginine, proline, alanine, glycine, mannitol, sorbitol, and/or glycerol. While not wishing to be bound by theory, the smaller chemical entity increases mobility, enabling the protein to relax to a lower energy state.

In one embodiment, the stabilizer is only sucrose, and the stabilizer makes up from about 3% to about 15%, preferably about 5-11%, 4-7.5%, or 5-7.5% of the weight of the pharmaceutically acceptable lyophilized cake, depending on the presence of other stabilizer components and the amount of protein, water, and other excipients. In an embodiment, the ratio of protein to stabilizer by weight is between 1:1-3:1, preferably 1.2:1-2:1, more preferably about 1.5:1.

In one embodiment, the stabilizer includes sucrose combined with another stabilizing agent. Those other stabilizing agents combined with sucrose include any one or more of arginine, sorbitol, mannitol, glycerol, and alanine. In one embodiment, the additional stabilizer comprises arginine, which may make up from about 4.83% to about 19.3% of the weight of the pharmaceutically acceptable lyophilized cake. In some embodiments, the weight to weight ratio of sucrose to arginine ranges from about 3.2:1 to about 3.4:1. In another embodiment, the additional stabilizer comprises sorbitol, which may make up from about 8.07% to about 22.4% of the weight of the pharmaceutically acceptable lyophilized cake. In another embodiment, the additional stabilizer comprises mannitol, which may make up from about 8.07% to about 22.4% of the weight of the pharmaceutically acceptable lyophilized cake. In another embodiment, the additional stabilizer comprises glycerol, which may make up from about 4.23% to about 12.7% of the weight of the pharmaceutically acceptable lyophilized cake. In yet another embodiment, the additional stabilizer comprises alanine, which may make up from about 4.11% to about 12.4% of the weight of the pharmaceutically acceptable lyophilized cake.

In another embodiment, the stabilizer comprises trehalose, which makes up from about 15.8% to about 70.2% of the weight of the pharmaceutically acceptable lyophilized cake, depending on the presence of other stabilizers and the amount of protein, water, and other excipients.

In one embodiment, the stabilizer comprises trehalose combined with another stabilizer. Those other stabilizers combined with trehalose include any one or more of arginine, sorbitol, mannitol, glycerol, and alanine. In one embodiment, the additional stabilizer comprises arginine, which may make up from about 0.81% to about 14.3% of the weight of the pharmaceutically acceptable lyophilized cake. In another embodiment, the additional stabilizer comprises sorbitol, which may make up from about 1.35% to about 22.4% of the weight of the pharmaceutically acceptable lyophilized cake. In another embodiment, the additional stabilizer comprises glycerol, which may make up from about 0.69% to about 12.7% of the weight of the pharmaceutically acceptable lyophilized cake. In yet another embodiment, the additional stabilizer comprises alanine, which may make up from about 0.69% to about 12.4% of the weight of the pharmaceutically acceptable lyophilized cake.

In another embodiment, the excipients comprise a surfactant. The surfactant may comprise a nonionic detergent, such as a fatty acylated polyethoxylated sorbitan. In one embodiment, the surfactant comprises a polysorbate generally, or specifically a polysorbate 80. The some embodiments, the pharmaceutically acceptable lyophilized cake comprises from about 0.21% to about 0.96% surfactant, such as polysorbate 80, by weight.

In one embodiment, the protein is a therapeutic protein. In another embodiment, the therapeutic protein is an antigen-binding protein. Antigen-binding proteins encompass a diverse group of molecules including antibodies, antibody fragments, receptors, ligands, recombinant molecules including complementarity determining regions, ligands, and receptor domains. Antigen-binding proteins include various other fusion (recombinant or chimeric) proteins such as receptor-Fc-fusion proteins, which include trap molecules. In a specific embodiment, the protein is a therapeutic antibody, such as a recombinant human-like or humanized monoclonal antibody. Antibodies include hybrid antibodies as well as bispecific antibodies.

In one embodiment, the protein represents from about 6.27% to about 63.7% of the weight of the pharmaceutically acceptable lyophilized cake. In some embodiments, the pharmaceutically acceptable lyophilized cake comprises from about 6.27% to about 18.9% protein by weight. In other embodiments, the pharmaceutically acceptable lyophilized cake comprises from about 33.4% to about 63.7% protein by weight.

Stabilizers are included in the pharmaceutically acceptable lyophilized cake to help maintain the stability of the protein. Therefore, the pharmaceutically acceptable lyophilized cake comprises particular ratios of stabilizer to protein. In some embodiments, the ratio of stabilizer to protein is about 0.22:1 to about 6.6:1 by weight. Various embodiments include stabilizer to protein ratios selected from 0.44:1, 0.65:1, 0.87:1, 1.1:1, and 1.3:1, all by weight.

The pharmaceutically acceptable lyophilized cake is contained. In some embodiments, the pharmaceutically acceptable lyophilized cake is contained in a closed vial. The closure may be a stopper. In other embodiments, the pharmaceutically acceptable lyophilized cake is contained in a syringe barrel. In still other embodiments, the pharmaceutically acceptable lyophilized cake is contained in one chamber of a dual chamber autoinjector.

In one embodiment, the pharmaceutically acceptable lyophilized cake is manufactured by combining a protein, a buffer, a nonionic surfactant, and one or more stabilizers in water to make a pre-lyophilized aqueous solution. The solution is then freeze-dried to make a cake containing no more than 10% and no less than 0.5% moisture. The freeze-dried (lyophilized) protein is in a "solid state." In a particular embodiment, the protein is a therapeutic recombinant human-like or humanized monoclonal antibody.

According to another aspect, a process for manufacturing a composition comprising a therapeutic protein and no more than 10% water and no less than 0.5% water is provided.

In one embodiment, the process includes the steps of obtaining an aqueous sample containing a protein and an excipient in a container. The container can be inter alia a vial, a syringe barrel, or a chamber of a dual chamber autoinjector. The container is sufficiently open to allow the outgassing of water vapor. The container containing the aqueous sample is placed into a chamber; heat is removed from the sample to attain a first temperature, wherein ice crystals form in the sample. Air is removed from the chamber to attain a first pressure. Thermal energy is then added to the sample to attain a second temperature to permit removal of the water from the sample by sublimation. Residual water may remain entrapped within the sample after sublimation, thereby requiring an additional second drying step. That second drying step is effectuated by adding thermal energy to the sample while maintaining the first pressure in the chamber, thereby attaining a third temperature. At that temperature, water is desorbed from the sample to attain a moisture level not greater than 10% and not less than 0.5%.

In one embodiment during the initial freezing and primary drying step, heat is removed from the aqueous sample at a rate of about 0.5° C. per minute. In one embodiment, the first temperature is about −45° C. In another embodiment, the first temperature is held for about 60 minutes. In yet another embodiment, the aqueous sample is held at 5° C. for about 30 minutes prior to attaining the first temperature.

In one embodiment, the primary drying step is conducted at a second temperature of about −25° C. In one embodiment, the second temperature is attained by increasing the shelf temperature at a rate of about 0.5° C. per minute. In one embodiment, the second temperature is held for about 50 hours. In one embodiment, the chamber pressure during primary drying is about 100 mTorr.

In one embodiment, the secondary drying step is conducted at a third temperature of about 35° C. In one embodiment, the ramp rate for heating is about 0.3° C. per minute. In one embodiment, the sample is held at the third temperature for about 6 hours.

After secondary drying, in one embodiment, the vial is stoppered at a chamber pressure of about 608,000 mTorr. In one embodiment, the chamber is backfilled with N2 gas prior to stoppering. In one embodiment, the vial is stoppered with a Flurotec® coated 4432/50 butyl rubber lyophilization stopper.

In one embodiment, the dried sample is annealed to relax the protein into a lower energy state and improve its overall stability. To anneal the sample, thermal energy is added to the sample to attain a fourth temperature. In some embodiments, the sample is held at the fourth temperature for at least about 24 hours, at least about 48 hours, or at least about 60 hours to achieve the optimal effective relaxation (alpha and beta relaxation) of the protein. Once the protein has attained its optimal state of relaxation, the container is closed.

In one embodiment, the fourth temperature, i.e., the annealing temperature is below the glass transition temperature of the sample after the water desorption step. In a specific embodiment, the annealing temperature is about 70° C. In another specific embodiment, the annealing temperature is about 45° C. In one embodiment, the sample is maintained at the annealing temperature for about 72 hours. Since different proteins have distinct biophysical characteristics, in some embodiments the fourth temperature is determined via modulated differential scanning calorimetry (MDSC). Here, the calorimeter is charged with a lyophilized protein formulation sample, which has been through the secondary drying step. The sample is then subjected to incremental heating through the glass transition while heat flow is monitored. The Tg is determined. Samples are then held at various sub-Tg temperatures for various times to induce enthalpic relaxation of the molecules in the lyophilization cake. The "relaxed" samples are then subjected to DSC or MDSC and the peak area (heat capacity as a function of temperature) due to enthalpic recovery is determined (see Luthra el al., "Effects of annealing on enthalpy relaxation in lyophilized disaccharide formulations: mathematical modeling of DSC curves," 97(8) J Pharm Sci. 3084-99, 2008; and L. Thomas, "Modulated DSC® Paper #5: Measurement of Glass Transitions and Enthalpy Recovery," TA Instruments Publication TP 010, New Castle Del., available for download on the world wide web at tainstruments.com (accessed May 13, 2016). Those sub-Tg temperatures and times that provide optimal enthalpic relaxation are selected for the fourth (a.k.a. annealing) temperature and time. See also W. Q., "Calorimetric analysis of cryopreservation and freeze-drying formulations," 1257 Methods Mol. Biol. 163-79 (2015).

In one embodiment, the pre-lyophilized aqueous solution (i.e., the aqueous sample, a.k.a. aqueous solution) comprises multiple excipients, such as one or more stabilizers, one or more buffers, and optionally one or more surfactants.

In one embodiment, the pre-lyophilized aqueous solution, as well as the reconstituted lyophilized liquid formulation, has a pH that assists in the maintenance of protein structure and function. In specific embodiments, the liquid pre-lyophilized and post-reconstituted liquid formulations have a pH of about 6.0±2. Molecules that buffer around pH 6 are considered useful in this embodiment. Thus in one embodiment, the buffer comprises histidine. In a specific embodiment, the aqueous solution contains about 10 mM histidine.

In one embodiment, the pre-lyophilized aqueous solution contains at least one stabilizer. In some embodiments, the stabilizer or combination of stabilizers includes one or more of trehalose, sorbitol, glycerol, arginine, alanine, mannitol, sucrose, proline, NaCl, and glycine.

In one embodiment, the stabilizer or combination of stabilizers includes sucrose. In a specific embodiment, the stabilizer comprises sucrose at a concentration of about 10% (w/v) in the aqueous solution. In one case, sucrose is the sole stabilizer. In another case, the aqueous solution comprises as a stabilizer about 3%±0.1% (w/v) arginine in addition to the 10% sucrose (w/v).

In other embodiments, the stabilizer comprises sucrose and at least one other molecular entity. In some embodiments, the aqueous solution comprises about 5% sucrose and one other stabilizer. In one specific embodiment, the aqueous solution comprises 5% sucrose and any one of (a) about 1.3%±0.1% (w/v) alanine, (b) about 1.5%±0.1% (w/v) arginine, (c) about 1.34%±0.1% (w/v) glycerol, (d) about 2.66%±0.1% (w/v) mannitol, and (e) about 2.66%±0.1% (w/v) sorbitol.

In some embodiments, the stabilizer comprises sucrose and arginine at various concentrations and proportions. In a specific embodiment, the aqueous solution comprises about 7.5% sucrose and 2.3%±0.1% arginine. In another specific embodiment, the aqueous solution comprises about 12.5% sucrose and 3.9%±0.1% arginine. In yet another specific embodiment, the aqueous solution comprises about 15% sucrose and 4.6%±0.1% arginine.

In some embodiments, the stabilizer comprises trehalose, either as the sole stabilizer, or combined with another stabilizer. In one embodiment, the stabilizer comprises trehalose at a concentration of about 10% (w/v) in the aqueous solution. In another embodiment, the aqueous solution comprises about 9.09% (w/v) trehalose and any one of 0.48% (w/v) sorbitol, 0.24% (w/v) glycerol, 0.28% (w/v) arginine, and 0.24% (w/v) alanine. In another embodiment, the aqueous solution comprises 8.33% (w/v) trehalose and any one of 0.89% (w/v) sorbitol, 0.45% (w/v) glycerol, 0.51% (w/v) arginine, and 0.43% (w/v) alanine. In another embodiment, the aqueous sample comprises 6.66% (w/v) trehalose and any one of 1.77% (w/v) sorbitol, 0.9% (w/v) glycerol, 1.03% (w/v) arginine, and 0.87% (w/v) alanine. In another embodiment, the aqueous sample comprises 5% (w/v) trehalose and any one of 2.66% (w/v) sorbitol, 1.34% (w/v) glycerol, 1.54% (w/v) arginine, and 1.3% (w/v) alanine.

A therapeutic protein of this process can be any therapeutic protein, including smaller peptides as well as larger proteins. In one embodiment, a therapeutic protein of the invention is greater than 100 kilodaltons, or about 150 kilodaltons or more. A therapeutic protein included in this invention may be an isolated endogenous protein, a heterologous expressed protein, and/or a recombinant protein, such as a chimeric fusion protein or a variant of an endogenous polypeptide. In one embodiment, a therapeutic protein is an antigen-binding protein. Antigen-binding proteins encompass any protein that binds to another molecular entity. For example, antigen-binding proteins include antibodies, bispecific antibodies, antibody fragments, ScFv fusion proteins, complementarity determining region (CDR)-containing proteins, ligands, receptors, ligand fragments, receptor fragments, fusion proteins comprising ligand and/or receptor domains, and receptor-Fc-fusion proteins, including trap molecules.

In one embodiment, the therapeutic protein is an antibody. In a specific embodiment, the therapeutic antibody is a monoclonal antibody. In a more specific embodiment, the therapeutic protein is a recombinant human-like or humanized antibody produced in a heterologous cell line. In another embodiment, the therapeutic protein is a receptor-Fc-fusion protein. In another more specific embodiment, the therapeutic protein is a trap molecule, such as an aflibercept molecule (VEGF trap) or a rilonacept molecule (IL-1 trap).

In some embodiments the antibody concentration in the aqueous solution is low, which includes a range of concentration greater than zero (i.e., as low or lower than 1 µg/mL)

and less than or equal to 25 mg/mL. In one low concentration embodiment, the antibody concentration is about 2 mg/mL.

In other embodiments the antibody concentration in the aqueous solution is medium, which includes a range of concentration greater than 25 mg/mL and less than or equal to 100 mg/mL. In one medium concentration embodiment, the antibody concentration is about 50 mg/mL.

In other embodiments the antibody concentration in the aqueous solution is high, which includes a range of concentration greater than 100 mg/mL and less than or equal to 200 mg/mL. In one high concentration embodiment, the antibody concentration is about 150 mg/mL.

In still other embodiments the antibody concentration in the aqueous solution is ultrahigh, which includes a range of concentration of antibody greater than 200 mg/mL. In one ultrahigh concentration embodiment, the antibody concentration is about 205 mg/mL.

As noted above, but without being limited to any mechanism of action, water can serve as a plasticizer for the lyophilized product, which surprisingly improves the stability of the protein. Thus in one embodiment, the moisture content of the manufactured composition (i.e., the stable lyophilized formulation) is ≥20% and ≤10% by weight. In another embodiment, the moisture content of the pharmaceutically acceptable lyophilized cake is ≥3% and ≤6% by weight. In another embodiment, the moisture content of the pharmaceutically acceptable lyophilized cake is ≥4% and ≤6% by weight. In one specific embodiment, the moisture content of the pharmaceutically acceptable lyophilized cake is about 6%. In another specific embodiment, the moisture content of the pharmaceutically acceptable lyophilized cake is about 4.5%. In yet another specific embodiment, the moisture content of the pharmaceutically acceptable lyophilized cake is about 3%.

In one embodiment, the lyophilized protein is stable for at least 24 months at room temperature. In a specific embodiment, ≤about 2% of a pharmaceutically acceptable lyophilized cake degrades following 24 months of storage at 25° C. Without being limited to any mechanism, degradation can involve proteolysis, chemical modification, aggregation, and the like. Aggregation is a common form of antibody degradation and is noticed by the formation of high molecular weight (HMW) species. Degradation can be determined using any protein analysis known in the art or yet to be invented. In a specific embodiment, the degradation of the antibody is determined by measuring the change in percent high molecular weight (HMW) species by size exclusion (SE) chromatography.

DRAWINGS

Figure 2:
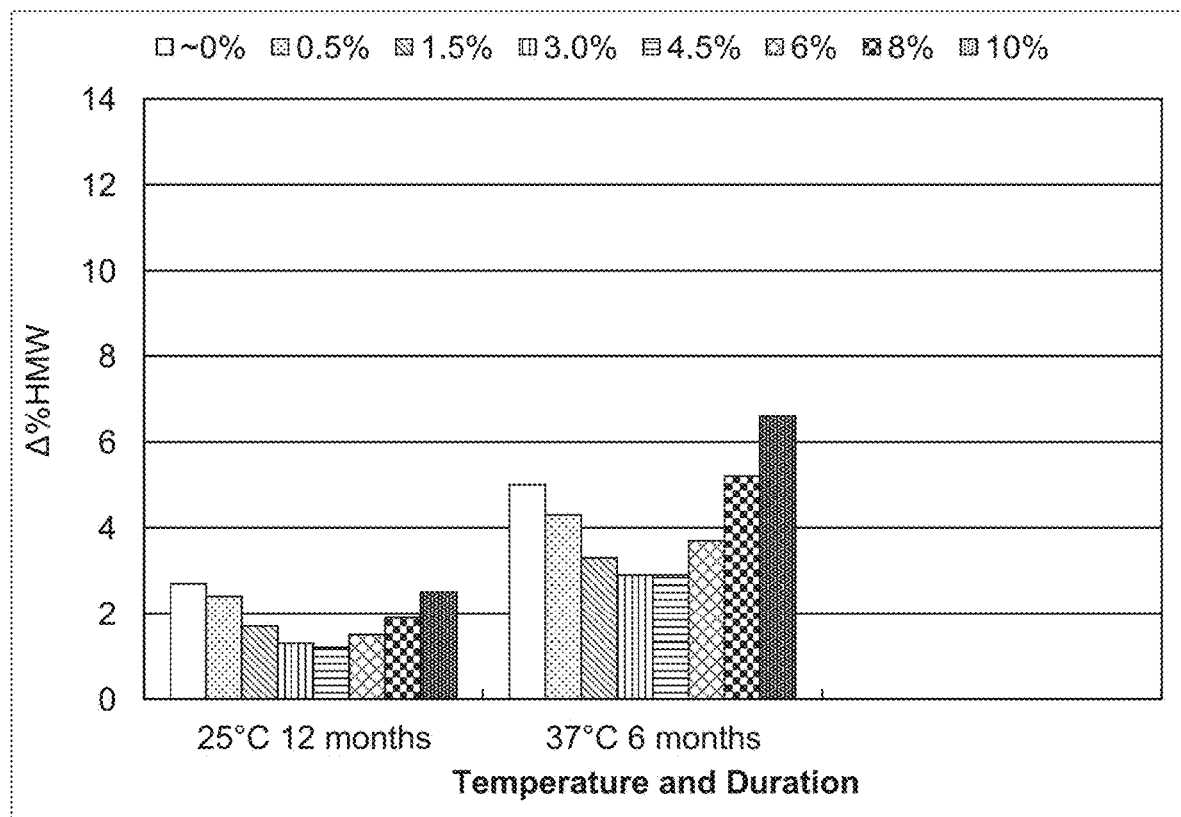

FIGS. 1 and 2 are bar graphs depicting the effect of temperature and moisture on protein stability over time. The X-axis depicts time in months and temperature. The Y-axis depicts the percent change in the amount of higher molecular weight species of protein. For each temperature, individual histograms represent increasing percent water content (w/w) from left to right along the X-axis, 0% water (open bars), 0.5% water (light shaded bars), 1.5° % water (downward cross hatch filled bars), 3.0% water (vertical line filled bars), 4.5% water (horizontal line filled bars), 6% water (open diamond filled bars), 8% water (checkered bars), and 10% water (dark shaded bars).

DETAILED DESCRIPTION

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Absolute amounts and relative amounts of excipients, ingredients, and other materials may be described by mass, or moles. Units of mass may be expressed as grams, milligrams, micrograms, and the like). The term "weight" as in "weight/volume" or "w/v" means "mass". Relative amounts may be expressed as percent weight (i.e., percent mass), wherein one (1) percent weight to volume (w/v) means 1 gram of material per 100 milliliter of volume. Also for example, one (1) part ingredient "A" per one (1) part ingredient "B" by weight means e.g. that for every one (1) gram of ingredient "A" there is one (1) gram of ingredient "B". Also for example, one percent (1%) by weight of ingredient "A" means e.g. that for every 100 grams of total mass of a particle there is one (1) gram of ingredient "A". Relative amounts of an ingredient may also be expressed in terms of moles or number of molecules per given volume, e.g., millimoles per liter (millimolar (mM)), or per other ingredient, e.g., X part ingredient "A" per Y part ingredient "B" by mole means for every X moles of "A" there are Y moles of "B"

Although any methods and materials similar or equivalent to those described herein can be used in the practice or testing of the present invention, the exemplar methods and materials are now described. All publications mentioned herein are incorporated herein by reference to describe in their entirety.

Excipients

An excipient is an ingredient added alongside an active drug substance in a pharmaceutical formulation. Excipients help to stabilize the drug substance and/or add bulk to the formulation. The term ingredient is used interchangeably with excipients.

Excipients include various substances for various purposes like buffering, bulking, solubilizing, stabilizing, plasticizing, and protecting the drug substance. Protectants protect against thermal stress and/or physical stress like agitation. Buffers are well known in the art.

In general, a buffer is included in the pre-lyophilzation aqueous protein solution to stabilize the protein before lyophilization and after reconstitution. The buffer may be included in the pre-lyophilization solution at a concentration of from 1 mM to 100 mM. In some particular embodiments, the buffer is included in the pre-lyophilization solution at about 10 mM. In certain embodiments, the buffer is present in the pre-lyophilization solution at a concentration of 5 mM±0.75 mM to 15 mM±2.25 mM; 6 mM±0.9 mM to 14 mM±2.1 mM; 7 mM±1.05 mM to 13 mM±1.95 mM; 8 mM±1.2 mM to 12 mM±1.8 mM; 9 mM±1.35 mM to 11 mM±1.65 mM; 10 mM±1.5 mM; or about 10 mM. In certain embodiments, the buffer system of the pre-lyophilization solution comprises histidine, phosphate, and/or acetate at 10 mM±1.5 mM.

In some embodiments, the buffer is selected from a chemical capable of buffering somewhere within the pH range of about 3 to about 9, or within the pH range of about 3.7 to about 8.0. For example, the pre-lyophilized solution may have a pH of about 3.4, about 3.6, about 3.8, about 4.0, about 4.2, about 4.4, about 4.6, about 4.8, about 5.0, about 5.2, about 5.4, about 5.6, about 5.8, about 6.0, about 6.2, about 6.4, about 6.6, about 6.8, about 7.0, about 7.2, about 7.4, about 7.6, about 7.8, or about 8.0.

The buffer may be a combination of individual buffers, such as, e.g., the combination of histidine and acetate (his-acetate buffer). In one embodiment, the buffer has a buffering range of about 3.5 to about 6, or about 3.7 to about 5.6, such as the range buffered by acetate. In one embodiment, the buffer has a buffering range of about 5.5 to about 8.5, or about 5.8 to about 8.0, such as the range buffered by phosphate. In one embodiment, the buffer has a buffering range of about 5.0 to about 8.0, or about 5.5 to about 7.4, such as the range buffered by histidine.

Excipients include stabilizers. As used herein, a stabilizer is added to the pre-lyophilized solution to stabilize the protein against aggregation or other degradation. Stabilization may occur via controlling the glass dynamics during the lyophilization process or by helping to preserve the native structure of the protein through specific interaction of the stabilizer with the protein. For a discussion of the biophysics of stabilizers during lyophilization, see Chang et al., "Mechanism of protein stabilization by sugars during freeze-drying and storage: native structure preservation, specific interaction, and/or immobilization in a glassy matrix?" 94(7) J. Pharm. Sci. 1427-44 (2005).

Stabilizers for inclusion in the pre-lyophilization solution include polyols, sugars, salts (e.g., sodium chloride), amino acids, and the like. Various individual stabilizers may be used alone or combined with one or more other stabilizers for optimal stabilizing effect. For example, a polyol may be combined with a sugar, a sugar with an amino acid, a polyol with an amino acid, a salt with a sugar, a salt with an amino acid, a salt with a polyol, and the like.

Polyols are organic molecules with more than one hydroxyl groups (—OH). Polyols include monomers as well as polymers. Sugar alcohols are a subgroup of polyols Sugar alcohols, which can serve as useful stabilizers, include mannitol, xylitol, sorbitol, isomalt, erythritol, maltitol, and glycerol. Other monomeric polyols include ethylene glycol, propylene glycol and pentaerythritol. Polymeric polyols may be polyesters or polyethers of polyol subunits. Useful exemplar polymeric polyols include polypropylene glycol, polyethylene glycol, and poly (tetramethylene ether) glycol.

Sugars are used as stabilizers (as well as bulking agents). Sugars can be categorized as either reducing or non-reducing sugars. Non-reducing sugars include the disaccharides sucrose and trehalose. Reducing sugars include glucose, maltose, and lactose. Generally, non-reducing sugars are preferred for protein lyophilization, since reducing sugars may reduce proteins via the mallard reaction. See generally Lavakumar et al., "Lyophilization/Freeze Drying—A Review," 3(4) Int. J. Novel Trends in Pharm. Sci. 2277-2782 (2013). The disaccharides trehalose and sucrose are relatively inert and tend to form an amorphous glass during lyophilization. Trehalose or sucrose, either alone or in combination with an amino acid or polyol, is used as a stabilizer in the practice of this invention.

In one embodiment, trehalose is used as the sole stabilizer. In other embodiments, trehalose is combined with a polyol. In some embodiments, the stabilizer is a combination of trehalose and sorbitol, or trehalose and glycerol. In other embodiments, the trehalose is combined with an amino acid. Specifically, trehalose is combined with alanine, or trehalose is combined with arginine.

In another embodiment, sucrose is used as the sole stabilizer. In other embodiments, the sucrose is combined with a polyol. In specific embodiments, the stabilizer is a combination of sucrose and mannitol, sucrose and sorbitol, or sucrose and glycerol. In other embodiments, the sucrose is combined with an amino acid. Specifically, sucrose is combined with arginine, or sucrose is combined with alanine.

Amino acids are used as stabilizers. Glycine is a commonly used bulking agent and stabilizer. Other useful amino acids include arginine, alanine, and proline. In some embodiments, arginine is used as a stabilizer. In some specific embodiments, arginine is combined with sucrose, or arginine is combined with trehalose. In other embodiments alanine is used as a stabilizer. In some specific embodiments, alanine is combined with sucrose, or alanine is combined with trehalose.

In some cases, one or more surfactants may be employed as an excipient. Surfactants are believed to provide additional stability by reducing protein-protein hydrophobic interaction and the resulting formation of high molecular weight species (i.e., aggregates). In some embodiments, one or more surfactant(s) may be included in the pre-lyophilized protein-containing aqueous solution. In other embodiments, one or more surfactant(s) may be included in the reconstitution diluent solution. Surfactants include substances which reduce the surface tension of a fluid in which it is dissolved and/or reduces the interfacial tension between oil and water. Surfactants can be ionic or non-ionic. Exemplary non-ionic surfactants that can be included in the pre-lyophilization solution or post reconstituted solution include, e.g., alkyl poly(ethylene oxide), alkyl polyglucosides (e.g., octyl glucoside and decyl maltoside), fatty alcohols such as cetyl alcohol and oleyl alcohol, cocamide MEA, cocamide DEA, and cocamide TEA. Specific non-ionic surfactants that can be included in the pre-lyophilized aqueous solution (or post reconstituted solution) include, e.g., polyoxyethylene sorbitan esters (a.k.a. polysorbates) such as polysorbate 20, polysorbate 28, polysorbate 40, polysorbate 60, polysorbate 65, polysorbate 80, polysorbate 81, and polysorbate 85; poloxamers such as poloxamer 188, poloxamer 407, polyethylene-polypropylene glycol; or polyethylene glycol (PEG). Polysorbate 20 is also known as TWEEN 20, sorbitan monolaurate and polyoxyethylenesorbitan monolaurate. Polysorbate 80 is also known as TWEEN 80, sorbitan monooleate and polyoxyethylenesorbitan monooleate.

The amount of surfactant contained within the pre-lyophilization solution or reconstitution solution may vary depending on the specific properties and purposes desired of the lyophilized formulation. In certain embodiments, the pre-lyophilization solution or reconstitution solution may contain about 0.001% (w/v) to about 0.5% (w/v) surfactant (e.g., polysorbate 20 or polysorbate 80). For example, the pre-lyophilization may contain about 0.001%; about 0.0015%; about 0.002%; about 0.0025%; about 0.003%; about 0.0035%; about 0.004%; about 0.0045%; about 0.005%; about 0.0055%; about 0.006%; about 0.0065%; about 0.007%; about 0.0075%; about 0.008%; about 0.0085%; about 0.009%; about 0.0095%; about 0.01%; about 0.015%; about 0.016%; about 0.017%; about 0.018%; about 0.019%; about 0.02%; about 0.021%; about 0.022%; about 0.023%; about 0.024%; about 0.025%; about 0.026%; about 0.027%; about 0.028%; about 0.029%; about 0.03%; about 0.031%; about 0.032%; about 0.033%; about 0.034%; about 0.035%; about 0.036%; about 0.037%; about 0.038%; about 0.039%; about 0.04%; about 0.041%; about 0.042%; about 0.043%; about 0.044%; about 0.045%; about 0.046%; about 0.047%; about 0.048%; about 0.049%; about 0.05%; about 0.051%; about 0.052%; about 0.053%; about 0.054%; about 0.055%; about 0.056%; about 0.057%; about 0.058%; about 0.059%; about 0.06%; about 0.061%; about 0.062%;

about 0.063%; about 0.064%; about 0.065%; about 0.066%; about 0.067%; about 0.068%; about 0.069%; about 0.07%; about 0.071%; about 0.072%; about 0.073%; about 0.074%; about 0.075%; about 0.076%; about 0.077%; about 0.078%; about 0.079%; about 0.08%; about 0.081%; about 0.082%; about 0.083%; about 0.084%; about 0.085%; about 0.086%; about 0.087%; about 0.088%; about 0.0890/0; about 0.09%; about 0.091%; about 0.092%; about 0.093%; about 0.094°%; about 0.095%; about 0.096%; about 0.097%; about 0.098%; about 0.099%; about 0.10%; about 0.15%; about 0.20%; about 0.25%; about 0.30%; about 0.35%; about 0.40%; about 0.45%; or about 0.50% surfactant (e.g., polysorbate 20 or polysorbate 80).

One or more plasticizers are included in the lyophilized protein composition. Plasticizers are generally used to increase the fluidity or flexibility of a system. It is thought that the increased fluidity is a result of the plasticizer increasing the free volume of the system and lowering the glass transition temperature. The addition of plasticizers modifies both alpha-relaxation and beta-relaxation within the lyophilized cake. Alpha-relaxation is also known as primary or glass relaxation and is a global relaxation process. Beta-relaxation is a more local process associated with protein polymer backbone motion that can be better modified by smaller molecules (i.e., plasticizers). Both relaxation processes reduce the overall energy of the system and, especially in the case of beta-relaxation, are thought to affect protein stability. It is generally known in the art of protein biophysics that plasticizers decrease beta-relaxation time and can concomitantly decrease protein stability (see e.g., Cicerone and Douglas, "β-Relaxation governs protein stability in sugar-glass matrices," Soft Matter 8: 2983-2991, 2012).

The invention also provides in an aspect lyophilized protein formulation embodiments containing one or more sugars combined with one or more plasticizers in a particular ratio to create a "stabilizer" that provides sufficient flexibility and alpha-relaxation to the cake, while preserving or enhancing protein stability. In some embodiments, the stabilizer comprises a weight-to-weight (i.e., mass-to-mass) ratio of sugar to plasticizer of about 19:1 to about 1:1. In some embodiments, the stabilizer comprises a weight-to-weight ratio of sugar to plasticizer of about 19:1, about 18:1, about 17:1, about 16:1, about 15:1, about 14:1, about 13:1, about 12:1, about 11:1, about 10:1, about 9:1, about 8:1, about 7:1, about 6:1, about 5:1, about 4:1, about 3:1, about 2:1, or about 1:1.

Useful plasticizers include polyols such as sorbitol, glycerol (glycerin), mannitol, and xylitol, amino acids such as glycine, arginine, proline, and alanine, and salts such as NaCl. Interestingly, water can also function as a plasticizer. However, water is generally disfavored because it is both a chemical reactant and plasticizer that leads to increased mobility and reduced Tg. Increased mobility correlates with increased reactivity and hydrolysis within the system. Increased reactivity and hydrolysis erodes protein stability. See Terakita et al., "The Influence of Water on the Stability of Lyophilized Formulations with Inositol and Mannitol as Excipients," 57(5) Chem. Pharm. Bull. 459-463 (2009).

As described above, mannitol, glycerol, sorbitol, and glycine in combination with water are used in some embodiments as a plasticizer. Not being bound by theory, these molecules in particular formulation embodiments are believed to decrease the beta-relaxation time while also increasing protein stability.

In some specific embodiments, the sugar sucrose or trehalose is combined with the plasticizer sorbitol in a weight-to-weight ratio of about 4:1, about 3.9:1, about 3.8:1, about 3.7:1, about 3.6:1, about 3.5:1, about 3.4:1, about 3.3:1, about 3.2:1, about 3.1:1, about 3:1, about 2.9:1, about 2.8:1, about 2.7:1, about 2.6:1, about 2.5:1, about 2.4:1, about 2.3:1, about 2.2:1, about 2.1:1, about 2:1, about 2:1, about 1.9:1, about 1.8:1, about 1.7:1, about 1.6:1, about 1.5:1, about 1.4:1, about 1.3:1, about 1.2:1, about 1.1:1, or about 1:1. In other specific embodiments, the sugar sucrose or trehalose is combined with the plasticizer arginine in a weight-to-weight ratio of about 33:1, about 32:1, about 31:1, about 30:1, about 29:1, about 28:1, about 27:1, about 26:1, about 25:1, about 24:1, about 23:1, about 22:1, about 21:1, about 20:1, about 19:1, about 18:1, about 17:1, about 16:1, about 15:1, about 14:1, about 13:1, about 12:1, about 11:1, about 10:1, about 9:1, about 8:1, about 7:1, about 6:1, about 5:1, about 4.5:1, about 4:1, about 3.5:1, or about 3:1.

The invention also provides in an aspect that water serves as a stabilizing plasticizer in the lyophilized composition and helps to reduce the rate of protein aggregation in lyophilized compositions stored at room temperature. The amount of moisture necessary to effectively stabilize the protein in the lyophilization cake at room temperature increases with increasing protein content, and decreases with decreasing protein content. Thus, a lyophilized composition derived from a pre-lyophilization solution containing 50 mg/mL of protein may require a lower moisture content than a lyophilized composition derived from a pre-lyophilization solution containing 150 mg/mL of protein. Also, the optimal amount of moisture needed to effectively stabilize the protein in the lyophilization cake changes with the storage temperature. For example, an intermediate amount of moisture is beneficial for long term storage of a protein lyophilizate at room temperature. At higher storage temperatures (e.g., 37° C.) less moisture is needed.

For example, FIG. 1 depicts the effect of moisture on stability of an exemplary antibody lyophilization formulation stored at 25° C., 37° C., or 50° C. Here, the pre-lyophilized formulation contained 150 mg/mL of an IgG, 5% sucrose, and 1.54% arginine. The final lyophilized cake contained moisture (w/w) at 0%, 0.5%, 1.5%, 3.0%, 4.5%, 6%, 8% or 10%. As shown in FIG. 1, higher storage temperature resulted in lower protein stability over 2 to 3 months. Interestingly, the optimal amount of moisture to convey maximum stability was higher at room temperature than at 37° C. or 50° C. In this particular example, the optimal moisture content for protein stability at room temperature was about 4.5% (w/w), and about 1.5% to about 3% for storage at 50° C. for 2 months. Longer term stability data is illustrated in FIG. 2, which depicts an exemplary antibody lyophilization formulation stored at 25° C. and 37° C. for 12 months and 6 months, respectively. As shown in FIG. 2, a moisture content of from 3.0% to 4.5% (w/w) conveyed the best stability under both temperatures tested, and a moisture content of 4.5% provided the greatest stability at 12 months under room temperature (25° C.) conditions.

In one embodiment, the invention provides a stable lyophilized protein (e.g., an antibody) formulation comprising from 1.5% to 8% water (w/w) that remains stable for at least 12 months at room temperature (25° C.), wherein stability refers to a less than 2% increase in high molecular weight species over the 12 month period of storage. In another embodiment, the invention provides a stable lyophilized protein (e.g., an antibody) formulation comprising from 3.0% to 4.5% water (w/w) that remains stable for at least 12 months at room temperature (25° C.), wherein stability refers to a less than 1.5% increase in high molecular weight species over the 12 month period of storage.

In some embodiments, the lyophilized composition contains ≥0.5% water by weight, ≥0.6% water by weight, ≥0.7% water by weight, ≥0.8% water by weight, ≥0.9% water by weight, ≥1% water by weight, ≥1.5% water by weight, ≥2% water by weight, ≥2.5% water by weight, ≥3% water by weight, ≥3.5% water by weight, ≥4% water by weight, ≥4.5% water by weight, ≥5% water by weight, ≥5.5% water by weight, ≥6% water by weight, ≥6.5% water by weight, ≥7% water by weight, ≥7.5% water by weight, ≥8% water by weight, ≥8.5% water by weight, ≥9% water by weight, or ≥9.5% water by weight, but no more than 10% water by weight. However, extra-optimal amounts of water may increase protein instability. Thus, in some embodiments the lyophilized composition contains ≤10% water by weight, ≤9.5% water by weight, ≤9% water by weight, ≤8.5% water by weight, ≤8% water by weight, ≤7.5% water by weight, ≤7% water by weight, ≤6.5% water by weight, ≤6% water by weight, ≤5.5% water by weight, ≤5% water by weight, ≤4.5% water by weight, ≤4% water by weight, ≤3.5% water by weight, ≤3% water by weight, ≤2.5% water by weight, ≤2% water by weight, ≤1.5% water by weight, ≤1% water by weight, ≤0.9% water by weight, ≤0.8% water by weight, ≤0.7% water by weight, ≤0.6% water by weight, but no less than 0.5% water by weight.

The phrase "moisture content" may be used interchangeably with "water content." However, "moisture content" is used to describe the water content of a lyophilized cake, whereas "water content" is used to describe the amount of water in an aqueous solution, gel, other liquid, gas, ice, or solid form of a formulation, such as a lyophilized cake, spray dried particle, and the like. In some embodiments, the moisture content of the lyophilized composition is between 0.5% and 10% by weight, between 1% and 10% by weight, between 2% and 10% by weight, between 3% and 10% by weight, between 4% and 10% by weight, between 5% and 10% by weight, between 6% and 10% by weight, between 7% and 10% by weight, between 8% and 10% by weight, between 9% and 10% by weight, between 0.5% and 9% by weight, between 0.5% and 8% by weight, between 0.5% and 7% by weight, between 0.5% and 6% by weight, between 0.5% and 5% by weight, between 0.5% and 4% by weight, between 0.5% and 3% by weight, between 0.5% and 2% by weight, between 0.5% and 1% by weight, between 1% and 2% by weight, between 1.5% and 2.5% by weight, between 2% and 3% by weight, between 2.5% and 3.5% by weight, between 3% and 4% by weight, between 3.5% and 4.5% by weight, between 4% and 5% by weight, between 4.5% and 5.5% by weight, between 5% and 6% by weight, between 5.5% and 6.5% by weight, between 6% and 7% by weight, between 6.5% and 7.5% by weight, between 7% and 8% by weight, between 7.5% and 8.5% by weight, between 8% and 9% by weight, between 8.5% and 9.5% by weight, between 9% and 10% by weight, between 9.5% and 10% by weight, or about 1%, 2%, 3%, 4%, 5%, 6%, 7% or 8% by weight. In some embodiments, the moisture content of the lyophilized composition is between 3% and 6% by weight; between 3.1% and 5.9% by weight, between 3.2% and 5.8% by weight, between 3.3% and 5.7% by weight, between 3.4% and 5.6% by weight, between 3.5% and 5.5% by weight, between 3.6% and 5.4% by weight, between 3.7% and 5.3% by weight, between 3.8% and 5.2% by weight, between 3.9% and 5.1% by weight, between 4% and 5% by weight, between 4.1% and 4.9% by weight, between 4.2% and 4.8% by weight, between 4.3% and 4.7% by weight, between 4.4% and 4.6% by weight, or about 4.5% by weight. In some embodiments, the moisture content of the lyophilized composition is between 2% and 4% by weight; between 2.1% and 3.9% by weight, between 2.2% and 3.8% by weight, between 2.3% and 3.7% by weight, between 2.4% and 3.6% by weight, between 2.5% and 3.5% by weight, between 2.6% and 3.4% by weight, between 2.7% and 3.3% by weight, between 2.8% and 3.2% by weight, between 2.9% and 3.1% by weight, or about 3% by weight.

In some embodiments, the percent water content by weight in the lyophilized cake is about 3%, about 3.1%, about 3.2%, about 3.3%, about 3.4%, about 3.5%, about 3.6%, about 3.7%, about 3.8%, about 3.9%, about 4%, about 4.1%, about 4.2%, about 4.3%, about 4.4%, about 4.5%, about 4.6%, about 4.7%, about 4.8%, about 4.9%, about 5%, about 5.1%, about 5.2%, about 5.3%, about 5.4%, about 5.5%, about 5.6%, about 5.7%, about 5.8%, about 5.9%, about 6%, about 6.1%, about 6.2%, about 6.3%, about 6.4%, about 6.5%, about 6.6%, about 6.7%, about 6.8%, about 6.9%, about 7%, about 7.1%, about 7.2%, about 7.3%, about 7.4%, about 7.5%, about 7.6%, about 7.7%, about 7.8%, about 7.9%, or about 8%. In some embodiments, the water content of the lyophilized cake is over 3% but less than 100% by weight.

Water content of the lyophilized cake may be determined by any one or more methods known in the art. Those methods include gravimetric methods, including thermogravimetry, gas chromatography, near-infrared spectroscopy, coulometry, and the Karl Fischer method or a relative humidity sensor method. Some of these methods are reviewed in J. K. Townes, "Moisture content in proteins: its effects and measurement," 705 J. Chromatography A 115-127, 1995; and Malik et al., "Analytical Options for the Measurement of Residual Moisture Content in Lyophilized Biological Materials," Am. Pharma. Rev. Aug. 1, 2010; and references cited therein. For example, the Loss on Drying (LOD) method (gravimetric) may be used in which the lyophilized cake is weighed, subjected to additional heating to completely drive off all water and other volatiles, and then weighed again. The loss of mass is attributed to water (and other volatiles) contained within the starting material. Another method to determine water content is the Karl Fischer method (volumetric or coulometric), which determines the amount of $H_2O$ by measuring the oxidation of $SO_2$ by $I_2$, wherein one mole of $I_2$ is consumer per mole of $H_2O$. Near-infrared spectroscopy measures reflectance from 1100 nm to 2500 nm through a glass vial (glass surface) containing the protein to determine moisture content without destroying the sample. See United States Pharmacopeia, XXIII Revision, USP Convention, Rockville, Md. 1995, pp. 1801-1802; and Savage et. al., "Determination of Adequate Moisture Content for Efficient Dry-Heat Viral Inactivation in Lyophilized Factor VIII by Loss on Drying and by Near Infrared Spectroscopy," 26 Biologicals 119-124, 1998.

Lyophilized Cake

A lyophilized composition containing a protein and stabilizer forms a solid matrix, also known as a "cake" or "lyophilized cake". A "pharmaceutically acceptable cake" (used interchangeably with or "pharmaceutically acceptable lyophilization cake") is amorphous (glassy, not crystalline) and has an aesthetically elegant appearance. The pharmaceutically acceptable cake should not show shrinkage, cracking, partial or total collapse, melt back, or discoloration. A red, black, brown, yellow, or other tinted cake is discolored and unacceptable. The ideal cake is mechanically strong and resistant to disruption during handling, porous and sponge-like, of uniform texture and forming a single entity, and uniformly white in color. The cake should be uniformly attached to the walls of the vial and not show detachment or other signs of shrinking. See Carpenter et al., "Rational design of stable lyophilized protein formulations: Some practical advice," Pharmaceutical Research, 14(8): 969-975, 1997.

The cake should be free of visual defects due to freezing problems including chimney-like structures; dried foam on the upper surface area; crusting or glazing on the cake surface; and horizontal layering or ring formation. The cake should also be free of visual defects due to drying problems including shrinkage, where the cake volume is smaller than the frozen matrix and signs of wall detachment are apparent; cracking, where the cake shows fissures in the dry matrix and the cake does not form a single entity; different degrees of cake structure loss, such as total or partial collapse of the cake; melt back, where the cake contains a ring of dissolved material in the lower region; partial melt back, where only a small region in the base of the cake contains dissolved material; and browning, which is a yellow or brown discoloration of the cake due to the inclusion of reducing sugar that has undergone the Maillard reaction. Melt back is particularly problematic since it can lead to slow dissolution times, protein aggregation, degradation, and loss of potency. See FDA, "Guide to Inspections of Lyophilization of Parenterals (7/93). Finished product inspection. Last update 2009," 2009, last accessed Jul. 8, 2016 from www.fda.gov/ICECI/Inspections/InspectionGuides/ucm074909.htm.

Protein Drug Substance

The term "protein" means any amino acid polymer having more than about 50 amino acids covalently linked via amide bonds. Proteins contain one or more amino acid polymer chains, generally known in the art as "polypeptides". A protein may contain one or multiple polypeptides to form a single functioning biomolecule. "Polypeptides" generally contain over 50 amino acids, whereas "peptides" generally contain 50 amino acids or less. Proteins may contain one or more covalent and non-covalent modifications. Disulfide bridges (i.e., between cysteine residues to form cystine) may be present in some proteins. These covalent links may be within a single polypeptide chain, or between two individual polypeptide chains. For example, disulfide bridges are essential to proper structure and function of insulin, immunoglobulins, protamine, and the like. For a recent review of disulfide bond formation, see Oka and Bulleid, "Forming disulfides in the endoplasmic reticulum," 1833(11) Biochim Biophys Acta 2425-9 (2013).

In addition to disulfide bond formation, proteins may be subject to other post-translational modifications. Those modifications include lipidation (e.g., myristoylation, palmitoylation, farnesoylation, geranylgeranylation, and glycosylphosphatidylinositol (GPI) anchor formation), alkylation (e.g., methylation), acylation, amidation, glycosylation (e.g., addition of glycosyl groups at arginine, asparagine, cysteine, hydroxylysine, serine, threonine, tyrosine, and/or tryptophan), and phosphorylation (i.e., the addition of a phosphate group to serine, threonine, tyrosine, and/or histidine). For a recent review on the post-translational modification of proteins produced in eukaryotes, see Mowen and David, "Unconventional post-translational modifications in immunological signaling," 15(6) Nat Immunol 512-20 (2014); and Blixt and Westerlind, "Arraying the post-translational glycoproteome (PTG)," 18 Curr Opin Chem Biol. 62-9 (2014).

Immunoglobulins (a.k.a. "antibodies") are examples of proteins having multiple polypeptide chains and extensive post-translational modifications. The canonical immunoglobulin protein (e.g., IgG) comprises four polypeptide chains, two light chains and two heavy chains. Each light chain is linked to one heavy chain via a cystine disulfide bond, and the two heavy chains are bound to each other via two cystine disulfide bonds. Immunoglobulins produced in mammalian systems are also glycosylated at various residues (e.g., at asparagine residues) with various polysaccharides, and can differ from species to species, which may affect antigenicity for therapeutic antibodies (see Butler and Spearman, "The choice of mammalian cell host and possibilities for glycosylation engineering", 30 Curr Opin Biotech 107-112 (2014)).

As used herein, "protein" includes therapeutic proteins, recombinant proteins used in research or therapy, trap proteins and other receptor Fc-fusion proteins, chimeric proteins, antibodies, monoclonal antibodies, human antibodies, bispecific antibodies, antibody fragments, nanobodies, recombinant antibody chimeras, cytokines, chemokines, peptide hormones, and the like. Proteins may be produced using recombinant cell-based production systems, such as the insect bacculovirus system, yeast systems (e.g., *Pichia* sp.), mammalian systems (e.g., CHO cells and CHO derivatives like CHO-KI cells). For a recent review discussing therapeutic proteins and their production, see Ghaderi et al., "Production platforms for biotherapeutic glycoproteins. Occurrence, impact, and challenges of non-human sialylation," 28 Biotechnol Genet Eng Rev. 147-75 (2012).

Some recombinant Fc-containing proteins contain receptors or receptor fragments, ligands or ligand fragments that have cognate binding partners in biological systems. "Receptor Fc-fusion proteins" refer to recombinant molecules that contain a soluble receptor fused to an immunoglobulin Fc domain. Some receptor Fc-fusion proteins may contain ligand binding domains of multiple different receptors. Those receptor Fc-fusion proteins are known as "traps" or "trap molecules". Rilonocept and aflibercept are examples of marketed traps that antagonize IL1R (see U.S. Pat. No. 7,927,583) and VEGF (see U.S. Pat. No. 7,087,411), respectively. Other recombinant Fc-containing proteins include those recombinant proteins containing a peptide fused to an Fc domain, for example Centocor's MIMETIBODY™ technology. Recombinant Fc-containing proteins are described in C. Huang, "Receptor-Fec fusion therapeutics, traps, and MIMETIBODY technology," 20(6) Curr. Opin. Biotechnol. 692-9 (2009).

"Fc-fusion proteins" comprise part or all of two or more proteins, one of which is an Fc portion of an immunoglobulin molecule, that are not fused in their natural state. For example, an Fc-fusion protein is a trap, such as for example an IL-1 trap (e.g., Rilonacept, which contains the IL-1RAcP ligand binding region fused to the IL-1R1 extracellular region fused to Fc of hIgGl; see U.S. Pat. No. 6,927,004, which is herein incorporated by reference in its entirety), or a VEGF Trap (e.g., Aflibercept, which contains the Ig domain 2 of the VEGF receptor Flt1 fused to the Ig domain 3 of the VEGF receptor Flkl fused to Fc of hIgGl; e.g., SEQ ID NO:1; see U.S. Pat. Nos. 7,087,411 and 7,279,159, which are herein incorporated by reference in their entirety).

In some embodiments, the protein is included in the pre-lyophilized aqueous solution at a concentration greater than 40 mg/mL. In some embodiments, the pre-lyophilized aqueous solution comprises protein at a concentration of about 50 mg/mL to about 250 mg/mL; about 100 mg/mL to about 200 mg/mL; about 125 mg/mL to about 175 mg/mL. In some embodiments, the pre-lyophilized aqueous solution comprises protein at a concentration of about 45 mg/mL, about 50 mg/mL, about 55 mg/mL, about 60 mg/mL, about 65 mg/mL, about 70 mg/mL, about 75 mg/mL, about 80 mg/mL, about 85 mg/mL, about 90 mg/mL, about 95 mg/mL, about 100 mg/mL, about 105 mg/mL, about 110 mg/mL, about 115 mg/mL, about 120 mg/mL, about 125 mg/mL, about 130 mg/mL, about 135 mg/mL, about 140 mg/mL, about 145 mg/mL, about 150 mg/mL, about 155 mg/mL, about 160 mg/mL, about 165 mg/mL, about 170 mg/mL, about 175 mg/mL, about 180 mg/mL, about 185 mg/mL, about 190 mg/mL, about 195 mg/mL or about 200 mg/mL.

Containers

In some embodiments, the pre-lyophilized aqueous solution containing the therapeutic protein is contained in a container. The freeze-drying process is applied to the solution in the vented container, which is subsequently closed to contain the freeze-dried composition. The term container is applied herein very broadly. The container for example may be a bulk container such as a bottle, jar or canister capable of containing from 2 mL to up to four liters or more, an ampoule, vial (glass or plastic), a syringe (glass or plastic), cartridge, or an autoinjector. The vial can be as small as 0.2 mL or less, or as large as 100 mL. Exemplar vials may be made of clear glass or amber glass, type I borosilicate glass, type II soda-silicate glass, or type III soda-silicate glass. The vial may be closed with a stopper, cap, flip cap, or a screw cap. SCHOTT®-style tubular glass is especially useful in lyophilization applications.

With the advent of biological drugs and patient self-administration of injectable drugs, autoinjectors have become a more important container for drug product. The self-administration of a lyophilized drug product requires that the patient reconstitute the lyophilized cake with sterile water for injection or other sterile solvent. To help ensure sterile reconstitution, volume control, ease of handling, and overall simplification, dual- or multi-chamber prefilled syringes can be used. Dual-chamber autoinjectors or other prefilled syringes contain the lyophilized drug product in one chamber and pre-measured amount of diluent or liquid pharmaceutical composition in another chamber. Exemplar dual chamber injectors are described at U.S. Pat. No. 6,149, 626 A, granted Nov. 21, 2006, and U.S. Pat. No. 7,959,600 B2, granted Jun. 14, 2011.

Protein Stability

The lyophilized form of the protein provides several advantages, one of which is maintaining the stability of the protein over time, especially for at least 18 months at room temperature. "Room temperature" refers to the temperature of a usual working environment. Room temperature includes temperatures within the range of 10-40° C., 17-27° C., 20-24° C., 25° C.±3° C., 25° C.±2° C., 25° C.±1° C., or about 25° C. The phrase "room temperature" may be used interchangeably with the phrase "ambient temperature." Room temperature encompasses "controlled room temperature", which indicates the temperature of a usual working environment of 20° C. to 25° C. with transient deviations (excursions) between 15° and 30° that may be experienced in pharmacies, hospitals, and warehouses. "Controlled room temperature" includes a calculated mean kinetic temperature of not more than 25° (see *The Pharmacopeia of the United States of America, Thirty-Third Revision and the National Formulary, Twenty-Eighth Edition*, USP 33-NF 28 Reissue, General Notices and Requirements, "Applying to Standards, Tests, Assays, and Other Specifications of the United States Pharmacopeia", § 10.30 Storage Temperature and Humidity, May 1, 2010, available at www.usp.org/sites/default/files/usp_pdf/EN/USPNF/USP33-NF28-ReissueGeneralNotices.pdf, last accessed Jul. 8, 2016).

The term "stability" refers to the retention of an acceptable degree of physical structure (thermodynamic and colloidal stability), chemical structure (kinetic stability), or biological function (functional stability) of the protein after storage in a relevant environment or under certain conditions. The protein may be stable even though it does not maintain 100% of its physical structure, chemical structure, or biological function after storage for a certain amount of time. Here for example, a lyophilized protein is considered stable when no more than 2% of the protein population is present in a high molecular weight form after storage at room temperature for up to 24 months. In some embodiments, a lyophilized or otherwise solid form of a protein is regarded as stable when about 3%, about 2.9%, about 2.8%, about 2.7%, about 2.6%, about 2.5%, about 2.4%, about 2.3%, about 2.2%, about 2.1%, about 2%, about 1.9%, about 1.8%, about 1.7%, about 1.6%, about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2% or about 0.1% or less of the protein is in a high molecular weight form after storage at room temperature for about 2 months, about 3 months, about 4 months, about 5 months, about 6 months, about 7 months, about 8 months, about 9 months, about 10 months, about 11 months, about 12 months, about 13 months, about 14 months, about 15 months, about 16 months, about 17 months, about 18 months, about 19 months, about 20 months, about 21 months, about 22 months, about 23 months, about 24 months, about 36 months or greater than 18 months.

Here, a lyophilized or other solid form of a protein is considered "unstable" at room temperature if the percent change in high molecular weight species is more than about 0.5%, more than about 0.6%, more than about 0.7%, more than about 0.8% or more than about 0.9% during the first month of storage at room temperature. Thus, a lyophilized or other solid form of a protein having a percent increase in high molecular weight species ≤0.5% during the first month of storage at room temperature may be regarded as stable.

Stability can be measured, inter alia, by determining the percentage of native molecule that remains in a formulation after storage for a defined amount of time at a defined temperature or after delivery to a patient. The percentage of protein that retains its native form (e.g., the portion of native species relative to total protein, including high molecular weight and low molecular weight species) can be determined by inter alia size exclusion chromatography (e.g., size exclusion high performance liquid chromatography [SE-HPLC]). In the case of a lyophilized protein, the cake is first solubilized and then the protein is subjected to testing. Native protein includes protein that is not aggregated or otherwise degraded. In certain embodiments, at least about 80%, 81%, 82%, 83%, 84%, 85%, 86%, 87%, 88%, 89%, 90%, 91%, 92%, 93%, 94%, 95%, 96%, 97%, 98%, 99% or 100% of the native form of the protein can be detected in the lyophilized cake after storage for a defined amount of time at a defined temperature. Greater than 80% of the protein in the lyophilized cake should be in its native form, and preferably over 90%. The defined amount of time after which stability is measured can be at least 14 days, at least 28 days, at least 1 month, at least 2 months, at least 3 months, at least 4 months, at least 5 months, at least 6 months, at least 7 months, at least 8 months, at least 9 months, at least 10 months, at least 11 months, at least 12 months, at least 13 months, at least 14 months, at least 15 months, at least 16 months, at least 17 months, at least 18 months, at least 19 months, at least 20 months, at least 21 months, at least 22 months, at least 23 months, at least 24 months, or more. The temperature at which the samples may be kept when assessing stability can be any temperature from about −80° C. to about 50° C., e.g., storage at about −80° C., about −30° C., about −20° C., about 0° C., about 4-8° C., about 5° C., about 25° C. or other room temperatures, about 35° C., about 37° C. or other physiological temperatures, about 45° C. or about 50° C.

Stability can be measured inter alia by determining the percentage of protein that forms an aggregate (i.e., high molecular weight species, a.k.a. HMW species) within the lyophilized cake after a defined amount of time at a defined temperature, wherein stability is inversely proportional to the percent high molecular weight (HMW) species that is formed. The percentage of HMW species of the protein may be determined by inter alia size exclusion chromatography after solubilization, as described above. A lyophilized protein composition may also be deemed stable if after three months at room temperature less than about 1%, 0.9%, 0.8%, 0.7%, 0.6%, 0.5%, 0.4%, 0.3%, 0.2% or 0.1% of the protein is detected in a HMW form.

Stability can be measured by determining the percentage of protein that is degraded or otherwise is found as a low molecular weight (LMW) species within the lyophilized cake after a defined amount of time at a defined temperature, wherein stability is inversely proportional to the percent LMW species that is detected in the solubilized lyophilized cake. The percentage of LMW species of the protein can be determined by size exclusion chromatography, as described above. A protein lyophilized cake may also be deemed stable if after three months at room temperature less than about 25%, 24%, 23%, 22%, 21%, 20%, 19%, 18%, 17%, 160%, 15%, 14%, 13%, 12%, 11%, 10%, 9%, 8%, 7%, 6%, 5%, 4%, 3%, 2%, 1%, 0.5%, or 0.1% of the first molecule is detected in a LMW form.

Other methods may be used to assess the stability of the lyophilized protein such as, e.g., differential scanning calorimetry (DSC) to determine thermal stability, controlled agitation to determine mechanical stability, and absorbance at about 350 nm or about 405 nm to determine solution turbidities. For example, a formulation of the present invention may be considered stable if, after 6 or more months of storage at about 5° C. to about 25° C., the change in $OD_{405}$ of the formulation is less than about 0.05 (e.g., 0.04, 0.03, 0.02, 0.01, or less) from the $OD_{405}$ of the formulation at time zero.

Stability may also be assessed by measuring the biological activity, physiological activity or binding affinity of the antibody or other protein to its target. For example, a lyophilized antibody may be regarded as stable if, after storage at e.g., 5° C., 25° C., 37° C., 45° C., 50° C., etc., for a defined amount of time (e.g., up to 1 month, 12 months, 18 months, 24 months, etc.), the antibody contained within the lyophilized formulation binds to its cognate epitope-containing antigen with an affinity that is at least 50%, 95%, or more of the binding affinity of the antibody prior to said lyophilization and storage. Binding affinity may be determined by, e.g., ELISA or plasmon resonance. Biological activity may be determined by an antibody, soluble receptor, or ligand activity assay, such as e.g., contacting a cell that expresses the cognate binding partner with the reconstituted formulation comprising the antibody, soluble receptor, or ligand. The binding of the antibody, soluble receptor, or ligand to such a cell may be measured directly, such as e.g., via FACS analysis. The protein may be considered "stable" when the biological or physiological specific activity (i.e., potency) of the protein is at least 50% of its initial (To) potency after storage at room temperature for at least 18 months. A stable protein retains at least 51% potency, at least 52% potency, at least 53% potency, at least 54% potency, at least 55% potency, at least 56% potency, at least 57% potency, at least 58% potency, at least 59% potency, at least 60% potency, at least 61% potency, at least 62% potency, at least 63% potency, at least 64% potency, at least 65% potency, at least 66% potency, at least 67% potency, at least 68% potency, at least 69% potency, at least 70% potency, at least 71% potency, at least 72% potency, at least 73% potency, at least 74% potency, at least 75% potency, at least 76% potency, at least 77% potency, at least 78% potency, at least 79% potency, at least 80% potency, at least 81% potency, at least 82% potency, at least 83% potency, at least 84% potency, at least 85% potency, at least 86% potency, at least 87% potency, at least 88% potency, at least 89% potency, at least 90% potency, at least 91% potency, at least 92% potency, at least 93% potency, at least 94% potency, at least 95% potency, at least 96% potency, at least 97% potency, at least 98% potency, or at least 99% potency after storage for up to 12 months, up to 13 months, up to 14 months, up to 15 months, up to 16 months, up to 17 months, up to 18 months, up to 19 months, up to 20 months, up to 21 months, up to 22 months, up to 23 months, or up to 24 months at room temperature.

A "stable" protein undergoes little or no change in structure or specific activity after storage at room temperature for a prolonged period of time, such as up to 18 months. Changes in structure include formation of aggregates or other high molecular weight forms of a protein, degradation of protein such as the hydrolysis of peptide bonds, and chemical degradation such as deamidation, asialylation, and the like. For example, a common form of antibody degradation is the formation of aggregates, which include reversible dimers and trimers, as well as more stable and less reversible tetramers and higher order multimers. "Irreversible aggregates" are a subset of aggregates that do not readily solubilize or dis-associate upon reconstitution of the lyophilized cake. A "stable" protein undergoes an increase in the formation of high molecular weight species that is less than 15%, less than 14%, less than 13%, less than 12%, less than 11%, less than 10%, less than 9%, less than 8%, less than 7%, less than 6%, less than 5%, less than 4%, less than 3%, less than 2%, less than 1%, or less than 0.5% during storage at room temperature for up to 7 months, up to 8 months, up to 9 months, up to 10 months, up to 11 months, up to 12 months, up to 13 months, up to 14 months, up to 15 months, up to 16 months, up to 17 months, up to 18 months, up to 19 months, up to 20 months, up to 21 months, up to 22 months, up to 23 months, or up to 24 months. Methods of detecting high molecular weight species may have a variability of detection of 0.2 to 0.3%.

The temperature-dependent rate of protein aggregation or other formation of high molecular weight species follows Arrhenius or modified-Arrhenius kinetics (slightly curved Arrhenius plots) (see for example Chakroun et al., "Mapping the Aggregation Kinetics of a Therapeutic Antibody Fragment," Mol. Pharmaceut. 13: 307-319 (2016)). Thus, aggregation rates and percent change in high molecular weight species at a given temperature for a given formulation over time can be predicted based upon a square root in time relationship and Arrhenius or modified-Arrhenius kinetics. For example, lyophilized samples are incubated at a given temperature (e.g., 5° C., 25° C., 37° C., 50° C.) in sealed glass vials. Aliquots are taken at regular intervals, insoluble aggregates removed, and then subjected to SE-HPLC. The observed rates of aggregation are determined directly from a linear fit of the time-dependent main peak versus HMW peak-area data. Projections of percent change in high molecular weight species are then made by applying a square root in time rate law and Arrhenius kinetics to the data. For example, the observed rate constant at various temperatures are then fitted to the Arrhenius equation: ln k=ln A−(E/RT), where E is the activation energy (in cal/mol), R is the Universal gas constant (1.987 cal/mol/K), T is the absolute temperature (in Kelvins) and ln A is a temperature constant that includes factors such as frequency of collisions. The value of k is extrapolated from the Arrhenius fit to predict the change in high molecular weight species at a given temperature (e.g., 25° C.) over time (e.g., 24 months).

Lyophilization

Methods of lyophilizing proteins in general and of therapeutic antibodies or other antigen-binding proteins in particular are well known in the art. Briefly, in one embodiment, lyophilization starts with a pre-lyophilized aqueous solution containing the drug substance and excipients, as described above. The pre-lyophilized aqueous solution is placed in an open container (e.g., vial) and the open container is placed into a lyophilization chamber onto a shelf. The lyophilization process comprises three basic steps: (1) freezing, with optional annealing cycles, (2) primary drying, and (3) secondary drying, with an optional post-drying annealing step. The first step is freezing. Here, the shelf temperature is lowered to cool the formulation in the vial. Ice crystals form within the formulation and the remainder of the formulation becomes more concentrated and viscous. The concentrated remainder solidifies to form an amorphous, crystalline, or combined crystalline/amorphous state. In one embodiment, the remainder solidifies in an amorphous glassy state.

In some lyophilization protocols, the frozen composition is subjected to annealing to enhance crystallization. The solid remainder is held at a temperature above the final freezing temperature for a period of time to crystallize some components, such as bulking agents like mannitol and glycine.

The ice is then removed by sublimation. The pressure of the lyophilization chamber (e.g., 40-400 Torr) and the shelf temperature (−30° C.-+10° C.) are adjusted below the triple point of water. The temperature is maintained below the glass transition temperature ($T_g$) for amorphous remainders to prevent collapse of the cake structure.

Some water may remain trapped within the matrix after the primary drying step. The remaining water is removed through the process of desorption during the secondary drying step. Here, the shelf temperature is increased to accelerate desorption and to attain the optimal moisture content in the lyophilized product. In one embodiment, the final moisture content is not less than about 0.5% and not more than about 10%. In another embodiment, the final moisture content is not less than about 3% and not more than about 6%. In a specific embodiment, the moisture content is more than 3% but less than 4%. In another specific embodiment, the moisture content is about 3%. In another specific embodiment, the moisture content is about 3.5%. In another specific embodiment, the moisture content is about 4%. In another specific embodiment, the moisture content is about 4.5%. In yet another specific embodiment, the moisture content is about 6%.

In one embodiment, the lyophilized product ("lyophilized cake") is subjected to an annealing step after the secondary drying step. Post-drying annealing is also referred to as physical aging or structural relaxation. This post-drying annealing step promotes relaxation of the amorphous matrix toward the equilibrium glassy state (alpha-relaxation), increasing the structural relaxation time at storage temperature, reducing mobility in the glass state, and likely lowering the protein to a more stable energy state, thereby optimizing protein stability. Here, the annealing step briefly accelerates molecular mobility to allow for an overall reduction of the entropy of the glassy state and the rotational forms of the protein.

After the annealing step, the number of random thermodynamic molecular states of the glass is minimized and the glass equilibrium is maximized. In some embodiments, the annealing temperature is below the Tg of the product. In some embodiments, the annealing temperature is from 25° C. to about 90° C., from 25° C. to about 80° C., from 25° C. to about 75° C., from about from about 25° C. to about 70° C., from 35° C. to about 70° C., from 40° C. to about 70° C., from 30° C. to about 55° C., from 50° C. to about 60° C., from 55° C. to about 65° C., from 60° C. to about 70° C., from 65° C. to about 75° C., from 70° C. to about 80° C., or from 75° C. to about 85° C. In some embodiments, the annealing temperature is about 90° C., about 80° C., about 79° C., about 78° C., about 77° C. about 76° C., about 75° C., about 74° C., about 73° C., about 72° C., about 71° C., about 70° C., about 69° C., about 68° C., about 67° C., about 66° C., about 65° C., about 64° C., about 63° C., about 62° C., about 61° C., about 60° C., about 59° C., about 58° C., about 57° C., about 56° C., about 57° C., about 56° C., about 55° C., about 54° C., about 53° C., about 52° C., about 51° C., about 50° C., about 49° C., about 48° C., about 47° C., about 46° C., about 45° C., about 44° C., about 43° C., about 42° C., about 41° C., about 40° C., about 39° C., about 38° C., about 37° C., about 36° C., about 35° C., about 34° C., about 33° C., about 32° C., about 31° C., about 30° C., about 29° C., about 28° C., about 27° C., about 26° C., or 25° C. In a specific embodiment, the annealing temperature is above 25° C. In another specific embodiment, the annealing temperature is above 50° C.

The lyophilized cake is held at the annealing temperature for a period of time sufficient to enable relaxation of the cake structure as defined by entherapy recovery from DSC or isothermic calorimetry. In some embodiments, the annealing temperature is held for about 12 hours to about two weeks, for from about 12 hours to one week, for about 12 hours to about several days, for about 18 hours to about 72 hours, for about 24 hours to about 36 hours, for about 30 hours to about 42 hours, for about 36 hours to about 48 hours, for about 42 hours to about 54 hours, for about 48 hours to about 60 hours, for about 54 hours to about 66 hours, for about 60 hours to about 72 hours, for about 66 hours to about 78 hours, or for about 72 hours to about 84 hours. In some embodiments, the annealing temperature is held for about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 25 hours, about 26 hours, about 27 hours, about 28 hours, about 29 hours, about 30 hours, about 31 hours, about 32 hours, about 33 hours, about 34 hours, about 35 hours, about 36 hours, about 37 hours, about 38 hours, about 39 hours, about 40 hours, about 41 hours, about 42 hours, about 43 hours, about 44 hours, about 45 hours, about 46 hours, about 47 hours, about 48 hours, about 49 hours, about 50 hours, about 51 hours, about 52 hours, about 53 hours, about 54 hours, about 55 hours, about 56 hours, about 57 hours, about 58 hours, about 59 hours, about 60 hours, about 61 hours, about 62 hours, about 63 hours, about 64 hours, about 65 hours, about 66 hours, about 67 hours, about 68 hours, about 69 hours, about 70 hours, about 71 hours, about 72 hours, about 73 hours, about 74 hours, about 75 hours, about 76 hours, about 77 hours, about 78 hours, about 79 hours, about 80 hours, about 81 hours, about 82 hours, about 83 hours, or about 84 hours.

In a specific embodiment, the annealing temperature is above 50° C., which is held for about 72 hours. In another specific embodiment, the annealing temperature is about 25° C., which is held for about 72 hours.

In one embodiment, the annealing conditions are determined experimentally by conducting a post-drying annealing step in a differential scanning calorimeter. An endothermic region of the temperature curve generally occurs immediately after the annealing effect, enabling the practitioner to select the annealing temperature. See Sartor et al., "Calorimetric Studies of the Kinetic Unfreezing of Molecular Motions in Hydrated Lysozyme, Hemoglobin, and Myoglobin," 66 Biophysical J. 249-258 (1994). Examples The following examples are put forth so as to provide those of ordinary skill in the art with a description of how to make and use the methods and compositions of the invention, and are not intended to limit the scope of the invention. Efforts have been made to ensure accuracy with respect to numbers used (e.g., amounts, sizes, etc.) but some experimental errors and deviations should be accounted for.

Example 1: Lyophilization Procedure

An aqueous pre-lyophilization solution containing antibody and excipients (as described herein) was loaded into Type I borosilicate glass vial. The charged vial was placed into a LYOSTAR 3 lyophilizer (SP Scientific, Warminster, Pa.). The chamber was closed and the shelf temperature reduced to 5° C. The sample was held at 5° C. for 30 minutes prior to freezing. The ramp rate for freezing was 0.5° C./min. The shelf temperature was held at −45° C. for 60 minutes.

Primary drying was performed at a vacuum set point of about 100 mTorr and a shelf temperature of about −25° C., which was attained with a ramp rate for heating of about 0.5° C./min, for about 50 hours.

Secondary drying was conducted at 35° C., which was attained at a ramp rate for heating of about 0.3° C./min. Secondary drying proceeded for about 6 hours.

After secondary drying, the chamber was backfilled with nitrogen gas to a pressure of about 0.8 atmospheres (about 608,000 mTorr), and the vial stoppered with a Flurotec® coated 4432/50 butyl rubber lyophilization stopper.

Example 2: Moisture Content Vs. Protein Stability

Water molecules may serve as a plasticizer and stabilizer in the lyophilized product. Water lends itself as a plasticizer due to its small size and ability to form hydrogen bonds with other water molecules and other molecules (such as protein molecules). An advantage to using water as a stabilizer/plasticizer is the ratio of stabilizer (water) to protein can be increased without affecting the tonicity of the reconstituted formulation. Moisture content can be adjusted through the design of the lyophilization process. Moisture content of the lyophilized cakes was determined by a Computrac® Vapor Pro® moisture analyzer (Arizona Instrument LLC, Chandler, Ariz.).

Recombinant monoclonal antibodies (mAb1, mAb2, mAb3) were produced in EESYR® cells (see U.S. Pat. No. 7,771,997 B2, issued on Aug. 10, 2010) and formulated at a concentration of 150 mg/mL in 10 mM histidine, pH 6.0, 0.1% polysorbate 80, 5% sucrose, and 1.54% arginine (all % w/v in pre-lyophilized liquid formulation). The liquid formulation was lyophilized as described above to specific levels of moisture content (% w/w), and stored at 50° C., 37° C., or 25° C. for specific times. After storage, the lyophilized formulations were reconstituted with water and subjected to size exclusion high pressure liquid chromatography (SE-HPLC). High molecular weight (HMW) species were detected, integrated and compared to controls at T=0. The percent change in HMW species as a portion of the total protein was calculated and reported in Table 1. Lyophilized 150 mg/mL mAb1 was the most stable with about 4.5% moisture content when stored at 25° C.

Lyophilized formulations of mAb1 having 3-10% moisture content were predicted to degrade ≤~2.0% following 24 months of 25° C. storage. Arrhenius kinetics algorithms were applied to measured degradation rates and projections based on a square root in time rate law were made out to at least 24 months. The percent change in HMW species for each moisture content point is reported in Table 2. The pre-lyophilized aqueous formulation was 150 mg/mL mAb1, 10 mM histidine, pH 6.0, 0.1% polysorbate 80, 5% sucrose, 1.54% arginine.

Example 3: The Effect of Post-Drying Annealing

Protein stability was improved by annealing the lyophilized drug product. Annealing the lyophilized formulation below the glass transition temperature is hypothesized to relax the amorphous molecules to a lower energy state resulting in a more stable product. Annealing the lyophilized formulation for 72 hours at 70° C. resulted in a lower observed increase in % HMW for 150 mg/mL mAb1 lyophilized with 10% sucrose and 3.08% arginine (Pre-lyo formulation: 150 mg/mL mAb1, 10 mM histidine, pH 6.0, 0.1% polysorbate 80, 10% sucrose, 3.08% arginine). The change in percent HMW species of antibody is reported in Table 3 for annealed and un-annealed formulations stored at 6 months at 25° C., 37° C., and 50° C.

TABLE 1

Percent Increase in High Molecular Weight Species

| | | Temp ° C. | | | | | | | |
|---|---|---|---|---|---|---|---|---|---|
| | | 50 | | | 37 | | | 25 | | |
| Time (months) | | 0.5 | 1 | 2 | 1 | 3 | 6 | 1 | 3 | 6 |
| % H$_2$O | 0 | 3.6 | 5.16 | 7.79 | 1.72 | 3.37 | 5.0 | 0.55 | 1.19 | 1.8 |
| | 0.5 | 3.1 | 4.42 | 6.84 | 1.48 | 2.91 | 4.3 | 0.51 | 1.02 | 1.6 |

TABLE 1-continued

Percent Increase in High Molecular Weight Species

| | Temp ° C. | | | | | | | | |
|---|---|---|---|---|---|---|---|---|---|
| | 50 | | | 37 | | | 25 | | |
| Time (months) | 0.5 | 1 | 2 | 1 | 3 | 6 | 1 | 3 | 6 |
| 1.5 | 2.4 | 3.56 | 5.54 | 1.07 | 2.19 | 3.3 | 0.31 | 0.7 | 1.1 |
| 3.0 | 2.3 | 3.38 | 5.46 | 0.88 | 1.77 | 2.9 | 0.26 | 0.55 | 0.9 |
| 4.5 | 2.7 | 3.77 | 6.18 | 0.91 | 1.86 | 2.9 | 0.22 | 0.46 | 0.7 |
| 6.0 | 2.1 | 4.6 | 7.75 | 0.9 | 2.33 | ND | 0.1 | 0.63 | ND |
| 8.0 | 2.9 | 5.8 | 10.67 | 1.4 | 2.98 | ND | 0.2 | 0.92 | ND |
| 10 | 3.6 | 7.0 | 13.29 | 1.8 | 4.14 | ND | 0.4 | 1.16 | ND |

TABLE 2

Degradation Prediction at 25° C. of 150 mg/mL Lyophilized mAb1 - Δ % HMW Species

| | Time | | | | | | |
|---|---|---|---|---|---|---|---|
| $H_2O$ | 1 mo | 3 mo | 6 mo | 9 mo | 12 mo | 18 mo | 24 mo |
| 0% | 0.77 | 1.33 | 1.89 | 2.31 | 2.67 | 3.24 | 3.77 |
| 0.5% | 0.66 | 1.14 | 1.61 | 1.97 | 2.27 | 2.78 | 3.21 |
| 1.5% | 0.47 | 0.82 | 1.16 | 1.42 | 1.64 | 2.01 | 2.32 |
| 3.0% | 0.36 | 0.63 | 0.89 | 1.09 | 1.26 | 1.54 | 1.78 |
| 4.5% | 0.31 | 0.55 | 0.77 | 0.94 | 1.09 | 1.34 | 1.54 |
| 6.0% | 0.34 | 0.60 | 0.84 | 1.03 | 1.19 | 1.46 | 1.69 |
| 8.0% | 0.49 | 0.85 | 1.20 | 1.47 | 1.70 | 2.08 | 2.41 |
| 10% | 0.64 | 1.11 | 1.58 | 1.93 | 2.23 | 2.73 | 3.15 |

Arrhenius kinetics algorithms were applied to measured degradation rates, and projections based on a square root in time rate law were made out to at least 24 months for annealed samples vs. un-annealed samples stored at 37° C. Annealing was projected to confer about 20% less HMW species than in the un-annealed sample at 24 months (i.e., 5.76% vs. 6.05% Δ % HMW).

TABLE 3

Δ % HMW with Annealing vs. without Annealing

| Temperature | Annealing | No Annealing |
|---|---|---|
| 25° C. | 0.2% | 0.6% |
| 37° C. | 0.5% | 1.5% |
| 50° C. | 0.8% | 2.1% |

Example 4: Individual Excipient Effects on Stability

Specific stabilizers including sugars, polyols, salts, and amino acids were assessed for their individual ability to stabilize the lyophilized antibody. Lyophilized 150 mg/mL mAb1 was the most stable when formulated with sucrose (see Table 4). The $T_g$ of the sucrose formulation is high enough (~110° C.) for room temperature storage and provides enough latitude for adding plasticizer if needed.

Example 5: Trehalose Combination Effects on Stability

Combining trehalose or sucrose with plasticizers such as sorbitol or mannitol surprisingly produced a more stable room temperature formulation. Combinations of sorbitol and trehalose stabilized lyophilized 150 mg/mL mAb1 more than trehalose alone. The base pre-lyophilized formulation was 150 mg/mL mAb1, 10 mM histidine, pH 6.0, 0.1% polysorbate 80, to which various combinations of trehalose and sorbitol were added prior to lyophilization. The stability of lyophilized protein combined with trehalose and/or sorbitol was tabulated as Δ % HMW in Table 5.

TABLE 4

Effect of Individual Excipients on mAb1 Δ % HMW

| | 50° C. @ 0.5 mo. | 50° C. @ 1 mo. | 50° C. @ 2 mo. | 25° C. @ 4 mo. |
|---|---|---|---|---|
| No stabilizer | 23.74 | 32.33 | 43.76 | 11.04 |
| 10% Sucrose | 2.68 | 4.12 | 6.24 | 0.87 |
| 10% Trehalose | 4.02 | 5.98 | 8.9 | 1.66 |
| 3.36% Proline | 9.08 | 13.48 | 19.52 | 3.79 |
| 5.32% Sorbitol | 8.29 | 12.45 | 18.32 | 1.83 |
| 5.32% Mannitol | 4.98 | 7.61 | 11.58 | 1.4 |
| 2.19% Glycine | 8.57 | 12.3 | 18.63 | 3.28 |
| 0.85% NaCl | 8.43 | 11.54 | 17.95 | 2.28 |
| 2.69% Glycerol | 12.86 | 17.34 | 25.91 | 4.49 |
| 3.08% Arginine | 6.66 | 10.06 | 14.86 | 2.95 |
| 2.60% Alanine | 9.84 | 14.58 | 22.23 | 4.03 |

TABLE 5

Effect of Trehalose and/or Sorbitol on mAb1 Δ % HMW

| | Stabilizer Combination | | | |
|---|---|---|---|---|
| | 10% Trehalose | 6.66% Trehalose, 1.77% Sorbitol | 5% Trehalose, 2.66% Sorbitol | 3.88% Trehalose, 3.55% Sorbitol |
| 25° C. (6 months) | 2.0% | 1.8% | 1.8% | 1.8% |
| 37° C. (6 months) | 5.4% | 5.0% | 5.1% | 5.6% |
| 50° C. (6 months) | 8.1% | 7.9% | 8.5% | 9.8% |
| 25° C. (24 months)* | 4.06% | 3.43% | 3.26% | 3.26% |

*Projections based on a square root, in time rate law and Arrhenius kinetics.

Example 6: Sucrose Combination Effects on Stability

Combinations of mannitol and sucrose stabilized lyophilized 150 mg/mL mAb1 more than sucrose alone. The base pre-lyophilized formulation was 150 mg/mL mAb1, 10 mM histidine, pH 6.0, 0.1% polysorbate 80, to which various combinations of sucrose and mannitol were added prior to lyophilization. The stability of lyophilized protein combined with sucrose and/or mannitol was tabulated as Δ % HMW in Table 6. The combination of mannitol and sucrose stabilized lyophilized 150 mg/mL mAb1 more than sucrose alone.

TABLE 6

Effect of Sucrose and Mannitol on mAb1 Δ % HMW

| | Stabilizer Combination | |
|---|---|---|
| | 10% Sucrose | 5% sucrose, 2.66% Sorbitol |
| 25° C. (6 months) | 1.6% | 1.3% |
| 37° C. (6 months) | 4.0% | 3.7% |
| 50° C. (2 months) | 5.9% | 7.2% |
| 25° C. (24 months)* | 2.86% | 2.52% |

*Projections based on a square root in time rate law and Arrhenius kinetics.

Sucrose was combined with polyols and amino acids to assess the ability to stabilize lyophilized antibody. 150 mg/mL mAb1 was combined with sucrose (Suc) and any one of sorbitol (Sor), glycerol (Gly), arginine (Arg), and alanine (Ala) in different proportions. Change in HMW species was assessed 25° C. and 5° C. at various storage times. The results (Δ % HMW) are presented in Table 7. None of the tested excipient combinations stabilized lyophilized 150 mg/mL mAb1 more than sucrose alone when stored at 25° C. Surprisingly, a combination of sorbitol and sucrose was predicted to improve stability over sucrose alone when stored at 5° C. for 120 months and is more stable than sucrose alone.

Example 7: Sucrose and Arginine Combination Effects on Stability of Drug Substance Lyophilized 150 mg/mL mAb1 and lyophilized 150 mg/mL mAb2 have comparable stability when formulated with 10° % sucrose and 3.08% arginine. Change in % HMW species were calculated at 1 month of storage at 25° C., 37° C., and 50° C. Lyophilized 150 mg/mL mAb1 and lyophilized 150 mg/mL mAb2 were predicted (based on a square root in time rate law and Arrhenius kinetics) to have comparable stability when formulated with 10% sucrose and 3.08% arginine at 25° C. out to 24 months and beyond. The results of Δ % HMW analysis are presented in Table 8.

TABLE 7

Effect of Other Excipients Combined with Sucrose on mAb1 Δ % HMW

| | 25° C./ 1 mo. | 25° C./ 3 mo. | 25° C./ 6 mo. | * 25° C./ 24 mo. | * 5° C./ 120 mo. |
|---|---|---|---|---|---|
| 10.0% Sucrose | 0.47% | 0.96% | 1.55% | 3.08% | 1.18% |
| 9.09% Suc/0.48% Sor | 0.53% | 1.04% | 1.60% | | |
| 8.33% Suc/0.89% Sor | 0.47% | 0.65% | 1.52% | | |
| 6.66% Suc/1.77% Sor | 0.46% | 0.98% | 1.53% | | |
| 5.00% Suc/2.66% Sor | 0.48% | 1.02% | 1.55% | 3.08% | 0.90% |
| 9.09% Suc/0.24% Gly | 0.52% | 1.06% | 1.66% | | |
| 8.33% Suc/0.45% Gly | 0.55% | 1.11% | 1.72% | | |
| 6.66% Suc/0.90% Gly | 0.65% | 1.27% | 2.05% | | |
| 5.00% Suc/1.34% Gly | 0.71% | 1.48% | 2.32% | 4.68% | 1.48% |
| 9.09% Suc/0.28% Arg | 0.51% | 1.02% | 1.61% | | |
| 8.33% Suc/0.51% Arg | 0.50% | 1.03% | 1.61% | | |
| 6.66% Suc/1.03% Arg | 0.57% | 1.14% | 1.83% | | |
| 5.00% Suc/1.54% Arg | 0.65% | 1.35% | 2.08% | 4.21% | 1.68% |
| 9.09% Suc/0.24% Ala | 0.50% | 0.99% | 1.58% | | |
| 8.33% Suc/0.43% Ala | 0.54% | 1.05% | 1.64% | | |
| 6.66% Suc/0.87% Ala | 0.65% | 1.30% | 1.91% | | |
| 5.00% Suc/1.30% Ala | 0.72% | 1.54% | 2.45% | 4.90% | 1.79% |

* Projections based on a square root in time rate law and Arrhenius kinetics.

TABLE 8

Effect of 10% Sucrose/3.08% Arginine on mAb1 and mAb2 Δ % HMW

| mAb1 | | | | mAb2 | | | |
|---|---|---|---|---|---|---|---|
| 25° C. (1 mo.) | 37° C. (1 mo.) | 50° C. (1 mo.) | *25° C. (24 mo.) | 25° C. (1 mo.) | 37° C. (1 mo.) | 50° C. (1 mo.) | *25° C. (24 mo.) |
| 0.2% | 0.5% | 1.5% | 0.97% | 0.1% | 0.5% | 1.5% | 0.71% |

*Projections based on a square root in time rate law and Arrhenius kinetics.

Example 8: Effect of Stabilizer to Drug Product Ratio on Drug Product Stability Combinations of sucrose and arginine were formulated with antibody at various proportions by weight and the Δ % HMW was determined at various times at 50° C. and 25° C. Lyophilized 150 mg/mL antibody formulations with ≥0.87:1 stabilizer to protein are predicted (based on a square root in time rate law and Arrhenius kinetics) to degrade ≤1% following 24 months of 25° C. storage. Results are listed in Table 9.

TABLE 9

Effect of Stabilizer to Protein Ratio on Stability (Δ % HMW)

| Sucrose/Arginine | Stabilizer:Antibody | 50° C. (0.5 mo) | 50° C. (1 mo) | 50° C. (2 mo) | *25° C. (24 mo) |
|---|---|---|---|---|---|
| 5%/1.5% | 0.44:1 | 3.7% | 5.4% | 8.2% | 3.74% |
| 7.5%/2.3% | 0.65:1 | 1.9% | 2.7% | 4.1% | 1.77% |
| 10%/3.1% | 0.87:1 | 1.0% | 1.5% | 2.3% | 0.97% |
| 12.5%/3.9% | 1.1:1 | 0.6% | 0.9% | 1.3% | 0.43% |
| 15%/4.6% | 1.3:1 | 0.4% | 0.6% | 0.9% | 0.35% |

*Projections based on a square root in time rate law and Arrhenius kinetics.

TABLE 10

Effect of Individual Excipients on mAb3 Δ % HMW

|  | 50° C. @ 0.5 mo. | 50° C. @ 1 mo. | 50° C. @ 2 mo. | 25° C. @ 7 mo. |
| --- | --- | --- | --- | --- |
| No stabilizer | 1.4% | 2.31% | 3.34% | 0.78% |
| 10% Sucrose | 0.03% | 0.03% | 0.04% | 0.04% |
| 10% Trehalose | 0.09% | 0.08% | 0.16% | 0.23% |
| 3.36% Proline | 2.0% | 2.92% | 12.37% | 3.25% |
| 5.32% Sorbitol | 3.5% | 6.24% | 8.85% | 1.47% |
| 5.32% Mannitol | 21.55% | 26.87% | 30.78% | 14.44% |
| 2.19% Glycine | 9.67% | 16.22% | 24.39% | 3.77% |
| 0.85% NaCl | 4.51% | 6.4% | 7.83% | 6.27% |
| 3.08% Arginine | 0.05% | 0.14% | 0.09% | 0.04% |
| 2.60% Alanine | 18.04% | 22.18% | 23.68% | 14.74% |

Example 9: Stabilizing Effect of Excipients on Lyophilized Protein on Low Protein Concentration in Pre-Lyophilized Liquid Formulation Specific stabilizers including sugars, polyols, salts, and amino acids were assessed for their individual ability to stabilize the lyophilized antibody. Lyophilized 2 mg/mL mAb3 showed no appreciable degradation when sucrose, trehalose or arginine was included as the stabilizer. Results are depicted in Table 10. Glycerol was also tested, but significant degradation was observed following lyophilization.

Trehalose was combined with polyols and amino acids to assess the ability to stabilize lyophilized antibody. 2 mg/mL mAb3 was combined with trehalose (Tre) and any one of sorbitol (Sor), glycerol (Gly), arginine (Arg), and alanine (Ala) in different proportions. Change in HMW species was assessed 25° C. various storage times. The results (Δ % HMW) are presented in Table 11. No appreciable degradation was observed in any of the 2 mg/mL mAb3 lyophilized formulations tested following 3 months of 25° C. storage

TABLE 11

Effect of Trehalose Plus Other Excipients on Low Concentration mAb3 Stability (Δ % HMW)

|  | 25° C./ 1 mo. | 25° C./ 3 mo. | *25° C./ 120 mo. |
| --- | --- | --- | --- |
| 10.0% Trehalose | 0.01% |  | 0.007% |
| 9.09% Tre/0.48% Sor |  | 0.03% |  |
| 6.66% Tre/1.77% Sor |  | 0.01% |  |
| 5.00% Tre/2.66% Sor | 0.01% |  |  |
| 5.00% Tre/1.34% Sor |  |  | 0.007% |
| 9.09% Tre/0.24% Gly | 0.01% |  |  |
| 5.00% Tre/1.34% Gly |  | 0.02% |  |
| 5.00% Tre/0.90% Gly |  |  | 0.10% |
| 9.09% Tre/0.28% Arg |  | 0.01% |  |
| 8.33% Tre/0.51% Arg | 0.04% | 0.01% |  |
| 6.66% Tre/1.03% Arg | 0.03% | 0.04% |  |
| 5.00% Tre/1.54% Arg | 0.05% | 0.05% | 0.33% |
| 9.09% Tre/0.24% Ala | 0.01% |  |  |
| 8.33% Tre/0.43% Ala | 0.08% | 0.08% |  |
| 6.66% Tre/0.87% Ala | 0.06% | 0.12% |  |
| 5.00% Tre/1.30% Ala | 0.04% | 0.2% | 1.03% |

*Projections based on a square root in time rate law and Arrhenius kinetics.

What is claimed is:

1. A lyophilized cake comprising:
   (a) a protein;
   (b) a stabilizer, wherein said stabilizer comprises about 5% sucrose by weight in the pre-lyophilized formulation and arginine in a weight to weight ratio of sucrose to arginine from about 3.2:1 to about 3.4:1;
   (c) a buffer; and
   (d) a moisture content of from about 3% to about 6% by weight,
   wherein the lyophilized cake is not collapsed.

2. The lyophilized cake of claim 1, wherein said lyophilized cake:
   (i) comprises no yellow, no brown, no black, and no red color;
   (ii) is not melted and comprises no density variation; and/or
   (iii) comprises a glass transition temperature above 25° C.

3. The lyophilized cake of claim 1, comprising a moisture content of from about 3.5% to about 5.5% by weight.

4. The lyophilized cake of claim 3, comprising a moisture content of about 4.5% by weight.

5. The lyophilized cake of claim 1, wherein said buffer comprises histidine at about 0.34% to about 2.04% by weight.

6. The lyophilized cake of claim 1, wherein said stabilizer is:
   (a) selected from the group consisting of a polyol, a sugar, an amino acid, a salt, and combinations thereof, wherein (i) said polyol is selected from the group consisting of sorbitol, glycerol, mannitol, and a combination thereof; (ii) said sugar is selected from the group consisting of trehalose, sucrose, and a combination thereof; (iii) said amino acid is selected from the group consisting of arginine, alanine, proline, glycine, and a combination thereof; and (iv) said salt is sodium chloride; and/or
   (b) present at about 19% to about 83% by weight.

7. The lyophilized cake of claim 1, wherein said stabilizer further comprises mannitol, wherein said mannitol is present at about 8% to about 23% by weight.

8. The lyophilized cake of claim 1, wherein said stabilizer further comprises sorbitol, wherein said sorbitol is present at about 1.3% to about 23% sorbitol by weight.

9. The lyophilized cake of claim 1 further comprising a surfactant, wherein:
   (a) said surfactant is selected from the group consisting of polysorbate 20, polysorbate 40, polysorbate 60, polysorbate 80, polyethylene glycol (PEG), PEG 3350, and a combination thereof; or
   (b) said surfactant is present at about 0.02% to about 1% by weight.

10. The lyophilized cake of claim 1, wherein said protein is present from about 6% to about 64% by weight.

11. The lyophilized cake of claim 1, wherein said protein is selected from the group consisting of an antigen-binding protein, an antibody, an antibody fragment, and a receptor-Fc-fusion protein.

12. The lyophilized cake of claim 1, wherein said lyophilized cake is contained within a vial, wherein said vial comprises type I borosilicate glass and is closed with a polytetrafluorethylene coated butyl rubber stopper.

13. A lyophilized cake comprising:
   (a) a protein;
   (b) a stabilizer at a ratio of about 0.2 parts stabilizer to 1 part protein by weight (0.2:1) to about 1.5 parts stabilizer to 1 part protein by weight (1.5:1), wherein said stabilizer comprises arginine, sorbitol, glycerol and/or alanine; and
   (c) a moisture content of from about 3% to about 6% by weight,
   wherein said lyophilized cake is free of discoloration.

14. The lyophilized cake of claim 13, wherein the ratio of the stabilizer to protein by weight is between about 0.22:1 and about 1.3:1 by weight.

15. The lyophilized cake of claim 13, wherein said stabilizer:
   (a) is selected from the group consisting of a non-reducing sugar, a sugar alcohol, an amino acid, and a combination thereof, wherein said non-reducing sugar comprises sucrose or trehalose; said sugar alcohol is selected from the group consisting of sorbitol, mannitol, and glycerol; and said amino acid is selected from the group consisting of arginine, alanine, proline, and glycine; or
   (b) comprises sucrose or trehalose.

16. The lyophilized cake of claim 15 (b) further comprising arginine, mannitol or sorbitol, wherein:
   (a) the ratio of sucrose to arginine is about 3.2:1 to about 3.4:1 by weight;
   (b) the ratio of sucrose to mannitol is about 1.8:1 to about 2:1 by weight;
   (c) the ratio of trehalose to arginine is about 3.2:1 to about 3.4:1 by weight; or
   (d) the ratio of trehalose to sorbitol is about 1:1 to about 2:1 by weight.

17. The lyophilized cake of claim 13, wherein said protein is selected from the group consisting of an antibody, an antibody fragment, and a receptor-Fc-fusion protein.

18. The lyophilized cake of claim 13, further comprising a buffer, wherein said buffer is selected from the group consisting of citrate, phosphate, histidine, succinate, carbonate, acetate, and a combination thereof.

19. The lyophilized cake of claim 13, wherein said lyophilized cake is contained within a vial or a syringe.

* * * * *